(12) United States Patent
Hattori et al.

(10) Patent No.: US 10,877,259 B2
(45) Date of Patent: Dec. 29, 2020

(54) MICROSCOPE SYSTEM, CULTURE-CELL ANALYSIS SYSTEM, AND METHOD OF MANAGING MICROSCOPIC IMAGE

(71) Applicant: OLYMPUS CORPORATION, Hachioji-shi, Tokyo (JP)

(72) Inventors: Toshiyuki Hattori, Tokyo (JP); Mina Kobayashi, Tokyo (JP); Naohiro Ariga, Tokyo (JP); Ayumu Sakurai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 144 days.

(21) Appl. No.: 16/038,632

(22) Filed: Jul. 18, 2018

(65) Prior Publication Data

US 2019/0025565 A1 Jan. 24, 2019

(30) Foreign Application Priority Data

Jul. 21, 2017 (JP) ................. 2017-141491
Jun. 5, 2018 (JP) ................. 2018-107907
Jul. 12, 2018 (JP) ................. 2018-132573

(51) Int. Cl.
*C12M 1/36* (2006.01)
*C12M 1/00* (2006.01)
(Continued)

(52) U.S. Cl.
CPC ........... *G02B 21/361* (2013.01); *C12M 41/14* (2013.01); *C12M 41/48* (2013.01); *G02B 21/24* (2013.01);
(Continued)

(58) Field of Classification Search
CPC .... A61K 2300/00; A61K 35/12; A61K 38/00; C12M 41/48; C12M 41/46; C12M 23/16;
(Continued)

(56) References Cited

U.S. PATENT DOCUMENTS 8,947,518 B2* 2/2015 Kiyota ............... G02B 21/0088
348/79
2005/0051723 A1* 3/2005 Neagle ................... C12M 41/14
250/306
(Continued)

FOREIGN PATENT DOCUMENTS

JP 2013201909 A * 10/2013

OTHER PUBLICATIONS

Machine translation of JP 2013-201909 A, translated Mar. 2, 2020, 9 pages. Retrieved: https://patents.google.com/patent/JP2013201909A/en?oq=jp+2013-201909 (Year: 2020).*
(Continued)

*Primary Examiner* — Andrew M Moyer
*Assistant Examiner* — Dennis Rosario
(74) *Attorney, Agent, or Firm* — Holtz, Holtz & Volek PC

(57) ABSTRACT

A microscope system includes a microscope apparatus configured to obtain a microscopic image of a culture cell by picking up an image of the culture cell, and a first control device configured to record a culture condition of the culture cell and the microscopic image in a recording unit in association with each other.

21 Claims, 27 Drawing Sheets

(51) Int. Cl.
  *G02B 21/36* (2006.01)
  *G02B 21/24* (2006.01)
  *G06K 9/00* (2006.01)
  *G02B 21/00* (2006.01)

(52) U.S. Cl.
  CPC ......... *G02B 21/365* (2013.01); *G02B 21/368* (2013.01); *G02B 21/0004* (2013.01); *G02B 21/367* (2013.01); *G06K 9/00127* (2013.01)

(58) Field of Classification Search
  CPC ...... C12M 41/14; C12M 41/36; C12M 41/12; C12Q 1/02; G01N 33/5008; G01N 33/5005; G01N 33/5011; C12N 2510/00; C12N 5/0696; C12N 15/85; C12N 5/0068; G06T 2207/30024; G06T 2207/10056; G06T 7/0012; G06T 7/0016; G06T 2207/30004; B01L 2200/0647; G06K 9/00127; G06K 2209/403; G02B 21/367; G02B 21/365; G02B 21/36; G02B 21/0088
  See application file for complete search history.

(56) References Cited

U.S. PATENT DOCUMENTS

| | | | |
|---|---|---|---|
| 2013/0038727 A1* | 2/2013 | Clark | C12M 41/48 348/143 |
| 2013/0183707 A1* | 7/2013 | Mangoubi | G06K 9/00147 435/29 |
| 2018/0320127 A1* | 11/2018 | Cannon | C12M 41/48 |
| 2019/0286908 A1* | 9/2019 | Shintani | G06K 9/00677 |
| 2019/0347798 A1* | 11/2019 | Koike | C12M 1/00 |

OTHER PUBLICATIONS

Kan et al., Proteome comparison of Vibrio cholerae cultured in aerobic and anaerobic conditions, Oct. 7, 2004 [retrieved Mar. 2, 2020], Proteomics, 4, pp. 3061-3067, Retrieved: https://onlinelibrary.wiley.com/doi/abs/10.1002/pmic.200400944 (Year: 2004).*

Kodama et al., Isolation and Characterization of a Sulfur-Oxidizing Chemolithotroph Growing on Crude Oil under Anaerobic Conditions, Jan. 2003 [retrieved Mar. 2, 2020], Applied & Environmental Microbiology, vol. 69, No. 1, pp. 107-112. Retrieved: https://aem.asm.org/content/69/1/107.short (Year: 2003).*

Baek et al., Time-Lapse Microscopy Using Smartphone With Augmented Reality Markers, Jan. 28, 2014 [retrieved Aug. 14, 2020], Microscopy Research & Technique, vol. 77, Issue 4, pp. 243-240. Retrieved: https://onlinelibrary.wiley.com/doi/full/10.1002/jemt.22335 (Year: 2014).*

Mitsuhi Hirata, et al., "Standardization of human embryonic stem (ES) cell and induced pluripotent stem (iPS) cells in Japan: Part3, Quality control," Tissue culture research communications, The Japanese Tissue Culture Association, 2011, vol. 30, pp. 145-157.

* cited by examiner

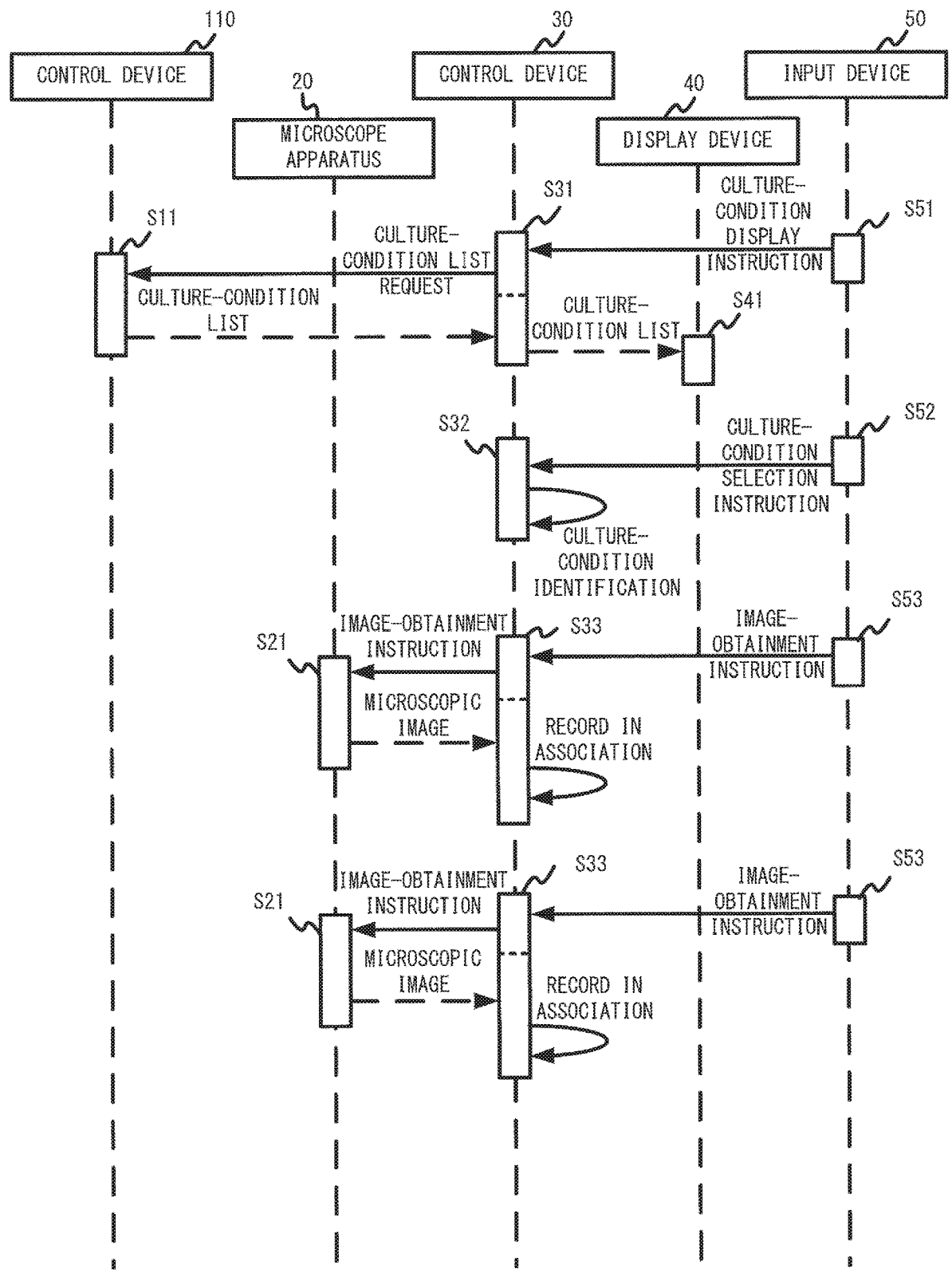
F I G. 3

TBi

| UUID | CELL NAME | CULTURE MEDIUM | CULTURE MEDIUM AMOUNT | NUMBER OF TIMES OF PASSAGE | DENSITY CHANGE |
|---|---|---|---|---|---|
| 65e18e30-230c-11e7-bffd-446655440000 | hESC | EB(-2Me) | 10ml | 10 | C:¥condition¥case1.tiff |
| 99c8d91d-2a3e-467f-9027-4f003c86e576 | hESC | EB(-2Me) | 10ml | 10 | C:¥condition¥case2.tiff |
| f98f7870-bd43-420b-aaf7-6b654eaaf29e | hESC | EB(-2Me) | 10ml | 8 | C:¥condition¥case3.tiff |
| a8cea38f-3311-4614-b2dc-bc86bcab084b | hESC | EB+2ME | 10ml | 10 | C:¥condition¥case4.tiff |

F I G. 5

TBm1

| CULTURE-CONDITION UUID | MICROSCOPIC-IMAGE UUID |
|---|---|
| 65e18e30-230c-11e7-bffd-446655440000 | 707fd6a9-8b1c-4feb-a187-cfa67aab5737 |

FIG. 8

TBm2

| CULTURE-CONDITION UUID | CELL NAME | CULTURE MEDIUM | CULTURE MEDIUM AMOUNT | NUMBER OF TIMES OF PASSAGE | DENSITY CHANGE |
|---|---|---|---|---|---|
| 65e18e30-230c-11e7-bffd-446655440000 | hESC | EB(-2Me) | 10ml | 10 | C:¥condition¥case1.tiff |

FIG. 9

TBm3

| MICROSCOPIC IMAGE UUID | MICROSCOPIC IMAGE (FLUORESCENCE) | MICROSCOPIC IMAGE (PHASE CONTRAST) |
|---|---|---|
| 707fd6a9-8b1c-4feb-a187-cfa67aab5737 | E:¥microscope¥imageF1.tiff | E:¥microscope¥imageP1.tiff |

FIG. 10

TBm1

| CULTURE-CONDITION UUID | MICROSCOPIC-IMAGE UUID |
|---|---|
| 65e18e30-230c-11e7-bffd-446655440000 | 707fd6a9-8b1c-4feb-a187-cfa67aab5737 |
| 65e18e30-230c-11e7-bffd-446655440000 | acd29896-66e1-43ec-a469-4a90b8418827 |
| 65e18e30-230c-11e7-bffd-446655440000 | e6a1626c-0f8e-4537-8d03-f54e82919cc3 |
| 65e18e30-230c-11e7-bffd-446655440000 | 49a62852-dcfa-406f-b933-e6ac89402d7c |
| ⋮ | ⋮ |
| 65e18e30-230c-11e7-bffd-446655440000 | 6103e1ff-e938-424c-a913-3402611c2d0b |

FIG. 11

TBi2

| UUID | CELL NAME | CULTURE MEDIUM | CULTURE MEDIUM AMOUNT | NUMBER OF TIMES OF PASSAGE | DENSITY CHANGE | USER ID | DATE |
|---|---|---|---|---|---|---|---|
| 65e18e30-230c-11e7-bffd-446655440000 | hESC | EB(-2Me) | 10ml | 10 | C:¥condition¥case1.tiff | b1234 | 2016/3/1 |
| 99c8d91d-2a3e-467f-9027-4f003c86e576 | hESC | EB(-2Me) | 10ml | 10 | C:¥condition¥case2.tiff | b4321 | 2016/2/1 |
| f98f7870-bd43-420b-aaf7-6b654eaaf29e | hESC | EB(-2Me) | 10ml | 8 | C:¥condition¥case3.tiff | b1234 | 2016/3/3 |
| a8cea38f-3311-4614-b2dc-bc86bcab084b | hESC | EB+2ME | 10ml | 10 | C:¥condition¥case4.tiff | a6543 | 2016/12/15 |

FIG. 12

TBm3

| MICROSCOPIC IMAGE UUID | MICROSCOPIC IMAGE (FLUORESCENCE) | MICROSCOPIC IMAGE (PHASE CONTRAST) |
|---|---|---|
| 707fd6a9-8b1c-4feb-a187-cfa67aab5737 | E:¥microscope¥imageF1.tiff | E:¥microscope¥imageP1.tiff |
| 65189288-25a1-41e0-8c15-e6f314baa238 | E:¥microscope¥imageF2.tiff | E:¥microscope¥imageP2.tiff |
| b1fb50d1-70ea-4aad-981a-9772baa8a304 | E:¥microscope¥imageF3.tiff | E:¥microscope¥imageP3.tiff |
| c9240b54-a421-4e67-b728-f406c137c256 | E:¥microscope¥imageF4.tiff | E:¥microscope¥imageP4.tiff |

FIG. 16

MICROSCOPE SYSTEM, CULTURE-CELL ANALYSIS SYSTEM, AND METHOD OF MANAGING MICROSCOPIC IMAGE

CROSS REFERENCE TO RELATED APPLICATIONS

This application is based upon and claims the benefit of priority from prior Japanese Patent Applications No. 2017-141491, filed Jul. 21, 2017, No. 2018-107907, filed Jun. 5, 2018, and No. 2018-132573, filed Jul. 12, 2018, the entire contents of which are incorporated herein by this reference.

BACKGROUND OF THE INVENTION

Field of the Invention

The disclosure of the present document is related to a microscope system, a culture-cell analysis sys, and a method of managing a microscopic image.

Description of the Related Art

In recent years, studies have actively developed to apply a human embryonic stem (ES) cell and an induced pluripotent stem (iPS) cell to the fields of regenerative medicine and drug development. Culture conditions including the culture medium, the lot of feeder cells, the timing of switching the passage or the culture media greatly influence the growth of these cells as described in for example Non-Patent Document 1 ("Standardization of human embryonic stem (ES) cell and induced pluripotent stem (iPS) cells in Japan: Part3, Quality control", Tissue culture research communications, The Japanese Tissue Culture Association, 2011, Vol. 30, pp 145-157 by HIRATA Mitsuhi, AHMAD Shandar, SUGA Mika, FUJIKI Ayaka, MATSUMURA Hiroko, WAKABAYASHI Mari, UEDA Naoko, LIU Kehong, HAYASHIDA Midori, HIRAYAMA Tomoko, KOHARA Arihiro, YANAGIHARA Kana, MIZUGUCHI Kenji, and K. FURUE Miho). Thus, the importance of the management of culture conditions is recognized in this field.

SUMMARY OF THE INVENTION

A microscope system according to an aspect of the present invention includes a microscope apparatus configured to obtain a microscopic image of a culture cell by picking up an image of the culture cell conveyed from an incubator, and a first control device configured to record a culture condition of the culture cell and the microscopic image in a recording unit in association with each other.

A culture-cell analysis system according to another aspect of the present invention includes the microscope system according to the above aspect and a culture monitoring system that includes the incubator and that monitors a culture status of the culture cell.

A method of managing a microscopic image according to another aspect of the present invention includes obtaining a microscopic image of a culture cell by picking up an image of the culture cell conveyed from an incubator, and recording a culture condition of the culture cell and the microscopic image in a recording unit in association with each other.

BRIEF DESCRIPTION OF THE DRAWINGS

The present invention will be more apparent from the following detailed description when the accompanying drawings are referenced.

FIG. 3 illustrates an example of a sequence diagram according to the first embodiment;
FIG. 5 illustrates an example of a culture-condition master table;
FIG. 8 illustrates an example of a link table;
FIG. 9 illustrates an example of a culture-condition table;
FIG. 10 illustrates an example of a microscopic-image table;
FIG. 11 illustrates another example of a link table;
FIG. 12 exemplifies another example of a culture-condition master table;
FIG. 16 illustrates another example of a microscopic-image table.

DESCRIPTION OF THE EMBODIMENTS

In the above studies, researchers analyze a culture cell through a microscope after taking out the culture cell from an incubator in which the culture environment (such as for example the temperature, the $CO_2$ concentration, and the pH) is managed. Such an analysis often includes a step in which the researcher observes the culture cell by viewing an image of the culture cell displayed on a display device, and the image of the culture cell is sometimes different from what the researcher expects.

In such a case, the cause of the difference should be identified. However, it is not easy for the researcher to identify the cause of the difference because the possibility includes various factors ranging from for example a factor due to the observation target (i.e., the culture cell itself), to the observation device (i.e., the microscope), and to other surrounding environments.

In view of the above, explanations will be given for the embodiments of the present invention.

Figure 1:
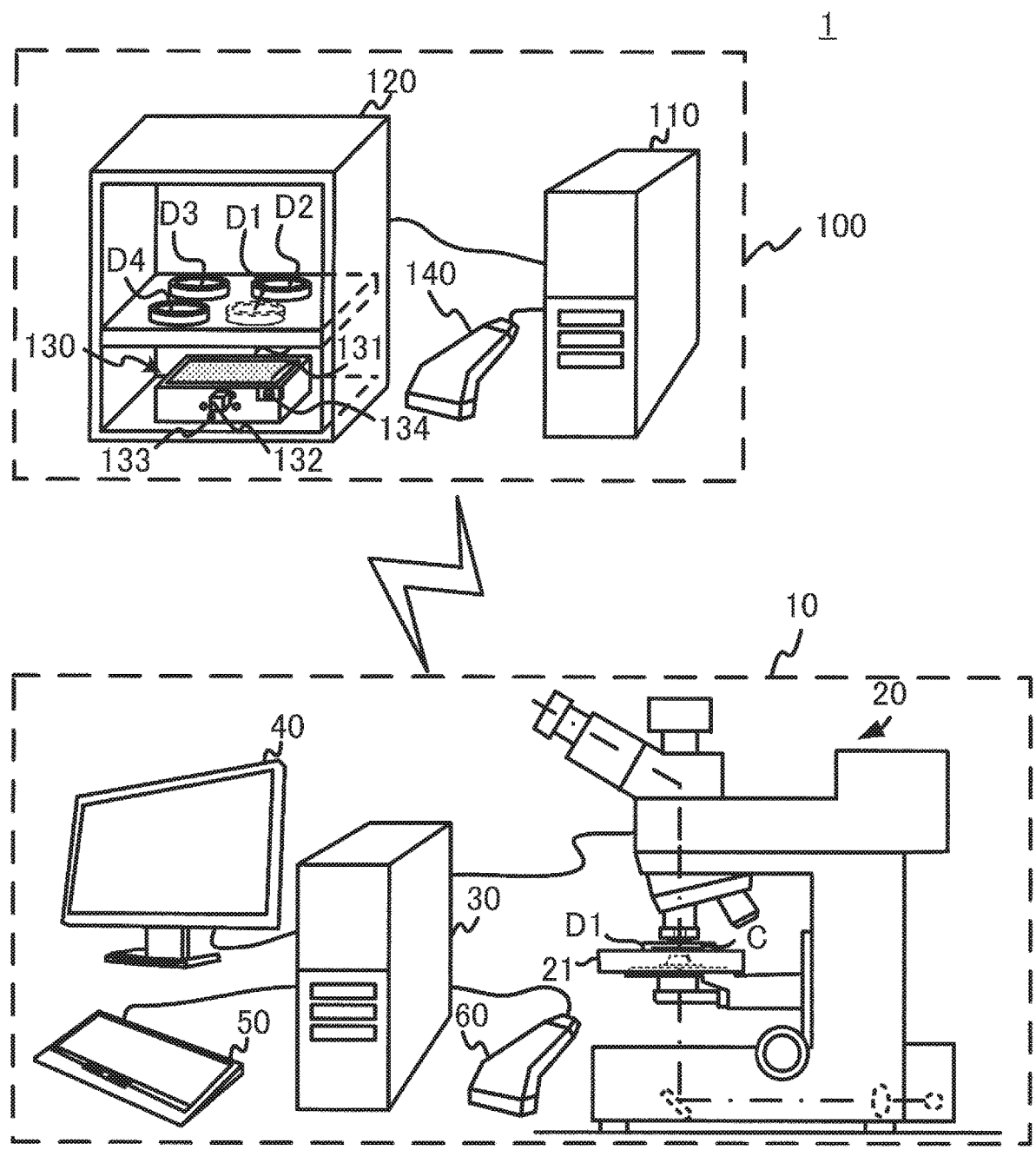
FIG. 1 exemplifies the configuration of a culture-cell analysis system 1.

FIG. 1 exemplifies the configuration of a culture-cell analysis system 1. The culture-cell analysis system 1 is a system to analyze a culture cell that has been cultured in a managed environment in an incubator 120. The culture-cell analysis system 1 analyzes a culture cell. The culture-cell analysis system 1 includes a culture monitoring system 100 and a microscope system 10.

The culture monitoring system 100 is a system to monitor the culture status of the culture cell. The culture monitoring system 100 includes a control device 110, the incubator 120 to culture the culture cell, and an image-pickup device 130 that is arranged in the incubator 120.

The control device 110 controls the image-pickup device 130 arranged in the incubator 120. In more detail, the control device 110 controls the image-pickup device 130 so that the image-pickup device 130 picks up an image of the culture cell arranged in the incubator 120. The control device 110 and the image-pickup device 130 are connected through a cable such as for example a USB (Universal Serial Bus) cable. However, the control device 110 and the image-pickup device 130 may be connected in an arbitrary configuration that allows mutual data communications, and may be connected in such a manner that wireless communications are possible.

The incubator 120 maintains or manages the culture environment. culture vessels (culture vessels D1 through D4) and the image-pickup device 130 are placed inside the incubator 120. Examples of a culture vessel may include a petri dish, a flask, and a microplate, although the invention is not limited to these examples. Each culture vessel contains a culture cell.

The image-pickup device 130 includes an image sensor 132, illumination-LED light sources 133, and a temperature sensor 134. Examples of the image sensor 132 may include a CCD (Charge-Coupled Device) image sensor and a CMOS (Complementary MOS) image sensor. The image sensor 132 and the plurality of illumination-LED light sources 133 are provided below an image-pickup area 131 in a freely movable manner. The temperature sensor 134 measures the temperature inside the incubator 120. Note that the incubator 120 may include another sensor to measure the environment inside the incubator 120.

The microscope system 10 includes a microscope apparatus 20 and a control device 30. The microscope system 10 may further include a display device 40 and an input device 50 as illustrated in FIG. 1.

The microscope apparatus 20 picks up an image of the culture cell conveyed from the incubator 120, and thereby obtains a microscopic image of the culture cell. FIG. 1 illustrates a situation where culture vessel D1 that contains culture cell C and that has been conveyed from the incubator 120 is mounted on a stage 21. The microscope apparatus 20 may be a fluorescence microscope or a phase-contrast microscope although the scope of the present invention is not limited to these examples. The microscope apparatus 20 may be a microscope other than these examples as well. In the following example, explanations will be given to an example in which the microscope apparatus 20 obtains both a fluorescence image and a phase-contrast image as microscopic images.

Note that when obtaining a microscopic image, culture cell C may be transferred, to a different sample vessel, such as a glass slide, that is suitable for a microscope observation, from conveyed culture vessel D1 instead of mounting the culture vessel D1 conveyed from the incubator 120 as it is on the stage 21 of the microscope apparatus 20.

The control device 30 controls the microscope apparatus 20. The control device 30 also executes various types of processes for analyzing the culture cell. Specifically, in order to assist the analysis of the culture cell and before the execution of the analysis process, the control device 30 performs an analysis preparation process in which a microscopic image obtained by the microscope apparatus 20 and the culture condition for the culture cell appearing in the microscopic image are recorded in the recording unit in association with each other. Note that the recording unit may be provided in the control device 30 or may be a device separate from the control device 30. For example, the recording unit may be a storage 33 (see FIG. 2), which will be described later. The recording unit may be a storage provided outside the control device 30 like for example a cloud server connected via a network. Note that specific examples of the analysis preparation process and the analysis process will be provided later.

The display device 40 is a display device that displays a window on the basis of data output from the control device 30. Examples of the display device 40 may include a liquid crystal display and an organic EL display.

The input device 50 inputs, to the control device 30, an instruction based on the user's manipulation. Examples of the input device 50 may include a mouse, a keyboard, and a touch panel. Note that the display device 40 and the input device 50 may be integrated or may be part of the control device 30.

The above culture-cell analysis system 1 includes two control devices (the control device 30 and the control device 110). When necessary, the control device 30 and the control device 110 will hereinafter be referred to as a first control device of the culture-cell analysis system 1 and a second control device of the culture-cell analysis system 1, respectively in order to distinguish these control devices.

Figure 2:
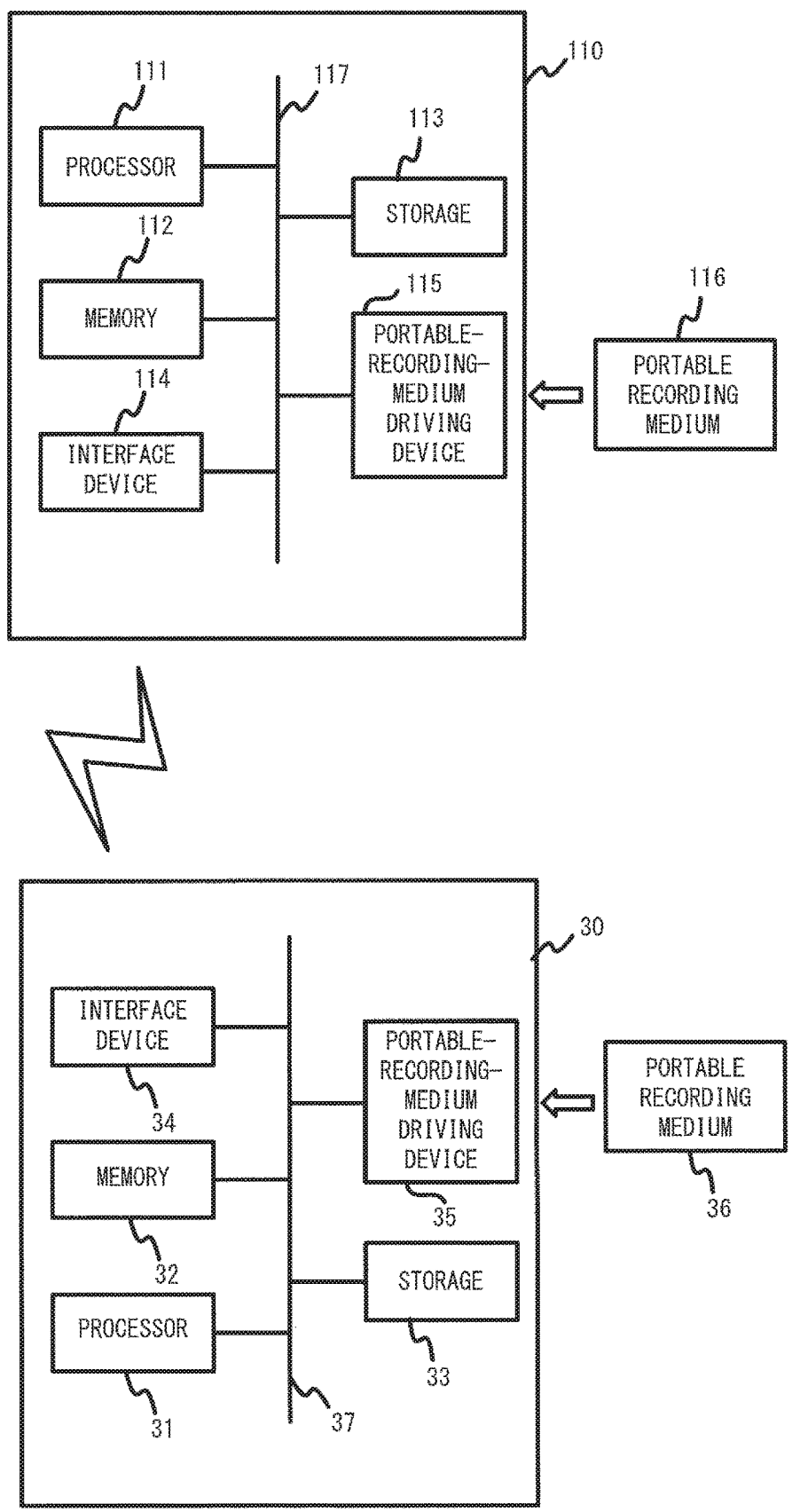
FIG. 2 exemplifies hardware configurations of a control device 110 and a control device 30.

FIG. 2 exemplifies hardware configurations of the control device 110 (the second control device) and the control device 30 (the first control device) both included in the culture-cell analysis system 1. The control device 110 and the control device 30 are for example standard computers.

As illustrated in FIG. 2, the control device 110 includes a processor 111, a memory 112, a storage 113, an interface device 114, and a portable-recording-medium driving device 115 into which a portable recording medium 116 is to be inserted, and they are connected to each other through a bus 117.

The processor 111 is for example a CPU (Central Processing Unit), an MPU (Micro Processing Unit), a DSP (Digital Signal Processor), etc., and executes a program to perform the programmed process. The memory 112 is for example a RAM (Random Access Memory), and temporarily stores a program or data stored in the storage 113 or the portable recording medium 116 upon the execution of the program.

The storage 113 is for example a hard disk or a flash memory, and is used mainly for storing various types of data and a program. The storage 113 includes for example culture-condition master table TBi built in it, and culture-condition master table TBi will be described later. The interface device 114 exchanges signals with a device (such as for example the incubator 120, the image-pickup device 130, the control device 30) that is not the control device 110. The portable-recording-medium driving device 115 accommodates the portable recording medium 116 such as for example an optical disk and a compact flash (registered trademark). The portable recording medium 116 has a function of assisting the storage 113. The storage 113 and the portable recording medium 116 are examples of a non-transitory computer-readable storage medium that has stored a program.

As illustrated in FIG. 2, the control device 30 includes a processor 31, a memory 32, a storage 33, an interface device 34, and a portable-recording-medium driving device 35 into which a portable recording medium 36 is to be inserted, and they are connected to each other through a bus 37.

The processor 31 is for example a CPU (Central Processing Unit), an MPU (Micro Processing Unit), a DSP (Digital Signal Processor), etc., and executes a program to perform the programmed process. The memory 32 is for example a RAM (Random Access Memory), and temporarily stores a program or data stored in the storage 33 or the portable recording medium 36 upon the execution of the program.

The storage 33 is for example a hard disk or a flash memory, and is used mainly for storing various types of data and a program. The storage 33 includes for example link table TBm1, culture-condition table TBm2, and microscopic-image table TBm3 built in it, and these tables will be described later. The interface device 34 exchanges signals with a device (such as for example the microscope apparatus 20, the display device 40, the input device 50, and the control device 110) that is not the control device 30. The portable-recording-medium driving device 35 accommodates the portable recording medium 36 such as for example an optical disk and a compact flash (registered trademark). The portable recording medium 36 has a function of assisting the storage 33. The storage 33 and the portable recording medium 36 are examples of a non-transitory computer-readable storage medium that has stored a program.

Note that the configurations illustrated in FIG. 2 are examples of the hardware configurations of the control device 30 and the control device 110, and the control device 30 and the control device 110 are not limited to these examples. The control device 30 and the control device 110 may be dedicated devices instead of general-purpose devices. The control device 30 and the control device 110 may include electric circuits such as for example an ASIC (Application Specific Integrated Circuit) and an FPGA (Field Programmable Gate Array) instead of or in addition to a processor that executes a program, and these electric circuits may perform an analysis preparation process and an analysis process, which will be described later. Hereinafter, processes performed in the culture-cell analysis system 1 will specifically be explained.

First Embodiment

Figure 4:
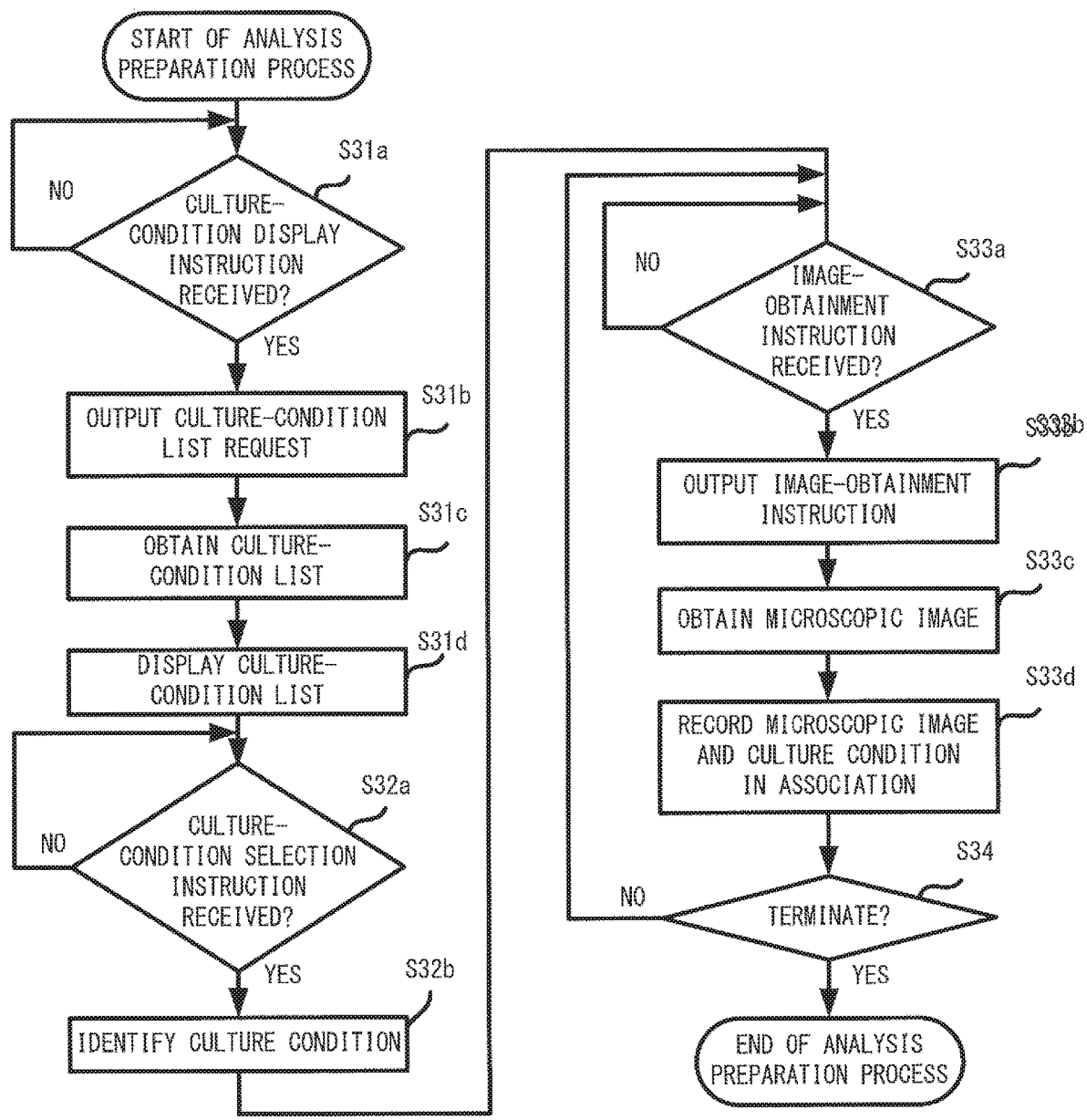
FIG. 4 illustrates an example of a flowchart of an analysis preparation process according to the first embodiment.
Figure 6:
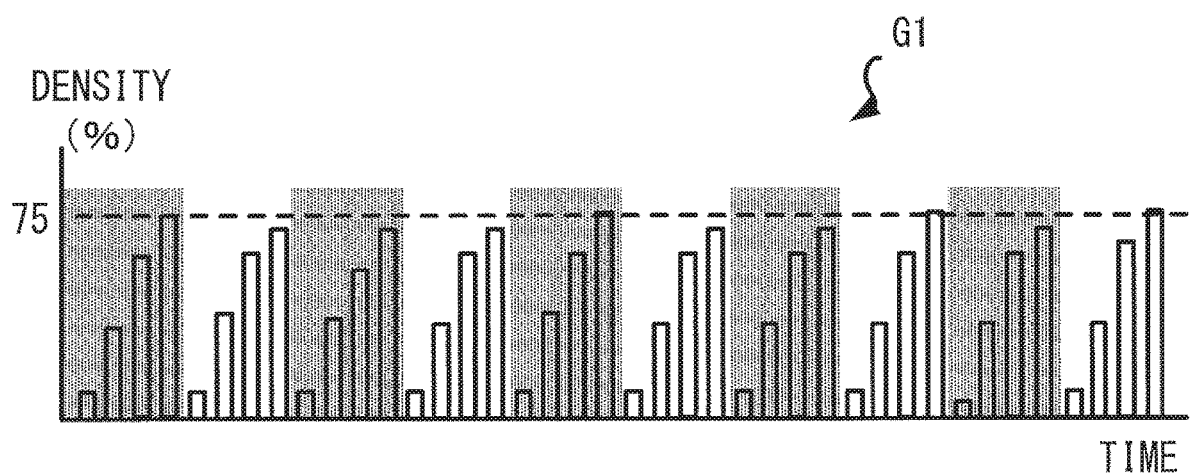
FIG. 6 illustrates an example of a graph illustrating temporal changes in the density.
Figure 7:
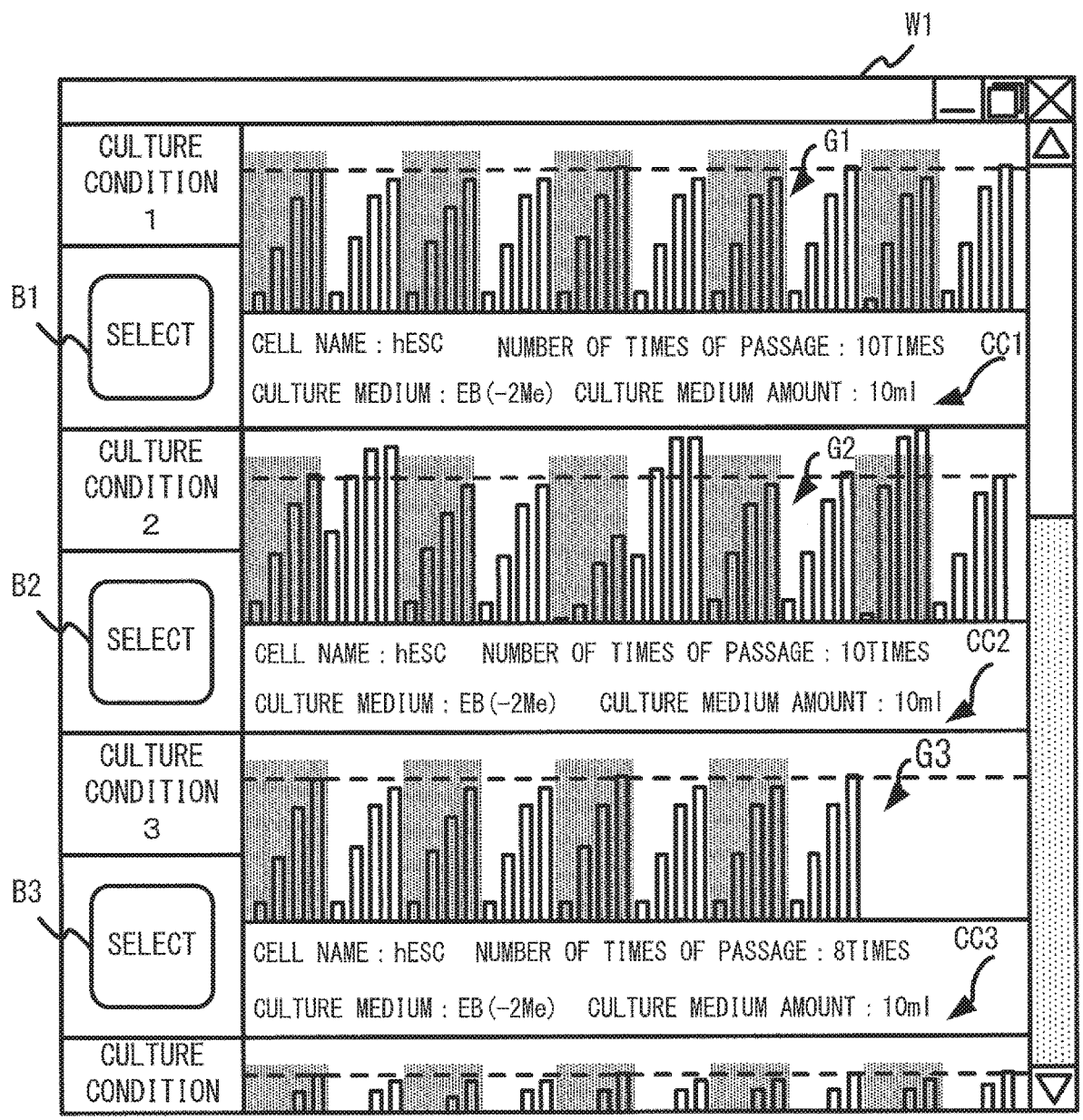
FIG. 7 illustrates an example of a culture-condition list window.

FIG. 3 illustrates an example of a sequence diagram according to the first embodiment. FIG. 4 illustrates an example of a flowchart of an analysis preparation process according to the first embodiment. FIG. 5 illustrates an example of a culture-condition master table. FIG. 6 illustrates an example of a graph illustrating temporal changes in the density. FIG. 7 illustrates an example of a culture-condition list window. FIG. 8 illustrates an example of a link table. FIG. 9 illustrates an example of a culture-condition table. FIG. 10 illustrates an example of a microscopic-image table. FIG. 11 illustrates another example of a link table. By referring to FIG. 3 through FIG. 11, explanations will be given for the analysis preparation process according to the present embodiment that is performed by the control device 30 of the culture-cell analysis system 1.

First, the user uses the input device 50 to input a culture-condition display instruction to the control device 30 (step S51). This starts the analysis preparation process illustrated in FIG. 4 in the control device 30.

When receiving the culture-condition display instruction from the input device 50 (YES in step S31a), the control device 30 outputs a culture-condition list request to the control device 110 (step S31b).

The control device 110 includes for example culture-condition master table TBi as illustrated in FIG. 5 built in it, and that culture-condition master table TBi records a culture condition calculated on the basis of an image obtained by the image-pickup device 130 for each culture vessel. In the table, the column "UUID" holds an identifier that uniquely identifies a culture condition. The columns of "cell name", "culture medium", "culture medium amount", and "number of times of passage" respectively hold the name of the culture cell being cultured in the culture vessel, the type of the culture medium, the amount of the culture medium, and the number of times of passage. The column "density change" holds the path to a graph image representing the temporal change in the density of the culture cell. Note that graph image G1 illustrated in FIG. 6 is an example of a graph image representing the temporal change in the density of the culture cell. FIG. 6 illustrates an example in which passage is being conducted when the density has increased to about 75%.

The control device 110 that has received a culture-condition list request outputs, to the control device 30, the culture-condition list read from culture-condition master table TBi (step S11). Specifically, in response to a request from the control device 30 serving as the first control device, the control device 110 serving as the second control device outputs, to the control device 30, the culture condition for culture cell C calculated on the basis of an image obtained by the image-pickup device 130. In the example illustrated in FIG. 5, four culture conditions are output as a list of culture conditions.

When obtaining the culture-condition list from the culture monitoring system 100 (the control device 110) (step S31c), the control device 30 stores the obtained culture conditions in the memory 32, and makes the display device 40 list the culture conditions (step S31d). Thereby, the display device 40 displays culture-condition list window W1 illustrated in FIG. 7 (step S41). The control device 30 may make the display device 40 display at least one of the obtained culture conditions instead of the list of them. In such a case, a different culture condition in accordance with the manipulation by the user may be displayed sequentially.

Culture-condition list window W1 illustrated in FIG. 7 is an example of a window that is generated on the basis of a culture-condition list and that is displayed by the display device 40, a culture-condition list being the control device 30 obtains from the control device 110. Window W1 illustrates, for each culture condition, a graph image (graph images G1 through G3) representing the temporal change in the density and character information (character information CC1 through CC3).

Next, the user uses the input device 50 to select, from among the culture conditions displayed in window W1, the culture condition corresponding to culture vessel (culture cell C) mounted on the stage 21 of the microscope apparatus 20, and thereby inputs a culture-condition selection instruction to the control device 30 (step S52). Herein, explanations will be given for an example in which "culture condition 1" has been selected with button B1 pushed in window W1.

When receiving the culture-condition selection instruction from the input device 50 (YES in step S32a), the control device 30 identifies, from among the culture conditions stored in the memory 32 (i.e., from among the culture conditions displayed on the display device 40), the culture condition selected by the user (step S32b). The culture condition identified in step S32b will hereinafter be referred to as a first culture condition.

Hereinafter, the user uses the input device 50 to input an image-obtainment instruction to the control device 30 (step S53).

When receiving the image-obtainment instruction from the input device 50 (YES in step S33a), the control device 30 outputs the image-obtainment instruction to the microscope apparatus 20 (step S33b).

The microscope apparatus 20 that has received the image-obtainment instruction picks up an image of culture cell C to obtain a fluorescence image and a phase-contrast image as microscopic images of culture cell C, and outputs the images to the control device 30 (step S21). Note that the microscopic image output to the control device 30 in step S21 is the first microscopic image that was obtained through the microscope apparatus 20 after the control device 30 identified the first culture condition.

After the identification of the first culture condition, the control device 30 obtains the first microscopic image from the microscope apparatus 20 (step S33c). Then the control device 30 records the obtained first microscopic image and the first culture condition identified in step S32b in association with each other (step S33d). The storage 33 of the control device 30 includes for example link table TBm1 illustrated in FIG. 8, culture-condition table TBm2 illustrated in FIG. 9, and microscopic-image table TBm3 illustrated in FIG. 10 built in it. In step S33d, the first microscopic image and the first culture condition that are to be recorded in association with each other are recorded in microscopic-image table TBm3 and culture-condition table TBm2, the UUIDs of the first microscopic image and the first culture condition are further recorded in link table TBm1, and thereby the first microscopic image and the first culture condition are associated with each other.

Lastly, the control device 30 determines whether to terminate the analysis preparation process (step S34). In this determination, the control device 30 determines not to terminate the analysis preparation process when a termination instruction has not been input from the input device 50, and repeats the processes in step S33a through step S34. Meanwhile, when a termination instruction has been input from the input device 50, the control device 30 terminates the analysis preparation process.

FIG. 11 illustrates a state of link table TBm1 after image-obtainment instructions were repeatedly input several times. In such a case, a culture condition recorded in association with the microscopic image during the repetition (first culture condition) does not change. Thus, a plurality of records having a UUID of an identical culture condition are recorded as illustrated in FIG. 11. Note that by performing an analysis preparation process again to select a different culture condition, a plurality of records including UUIDs of different culture conditions are recorded in link table TBm1.

As described above, performing an analysis preparation process according to the present embodiment makes it possible for the microscope system 10 to record a microscopic image and a culture condition in association with each other, the microscopic image being obtained by the microscope apparatus 20 and the culture condition being managed by the culture monitoring system 100. This makes it easy for the user to identify the culture condition for a culture cell appearing in a microscopic image when the culture cell is to be analyzed. The microscope system 10 and the culture monitoring system 100 according to the present embodiment thus can assist the analysis of a culture cell by for example making it easy to determine whether the culture condition has influenced an image of the culture cell when the image of the culture cell is different from the expected image.

Also, the analysis preparation process according to the present embodiment requires less labor of the user for associating a microscopic image obtained after the selection of a culture condition and the selected culture condition because they are associated automatically. Thereby, the association can be conducted without imposing an excessive burden on the user.

Note that the configuration of culture-condition master table TBi is not limited to the example illustrated in FIG. 5. For example, it may include columns of "user ID" and "date" similarly to culture-condition master table TBi2 illustrated in FIG. 12. The column "user ID" holds an identifier for identifying a user who has registered the culture condition of each record (each row) in culture-condition master table TBi2. The column "date" holds a date at which the culture condition of each record (each row) was registered in culture-condition master table TBi2.

Figure 13:
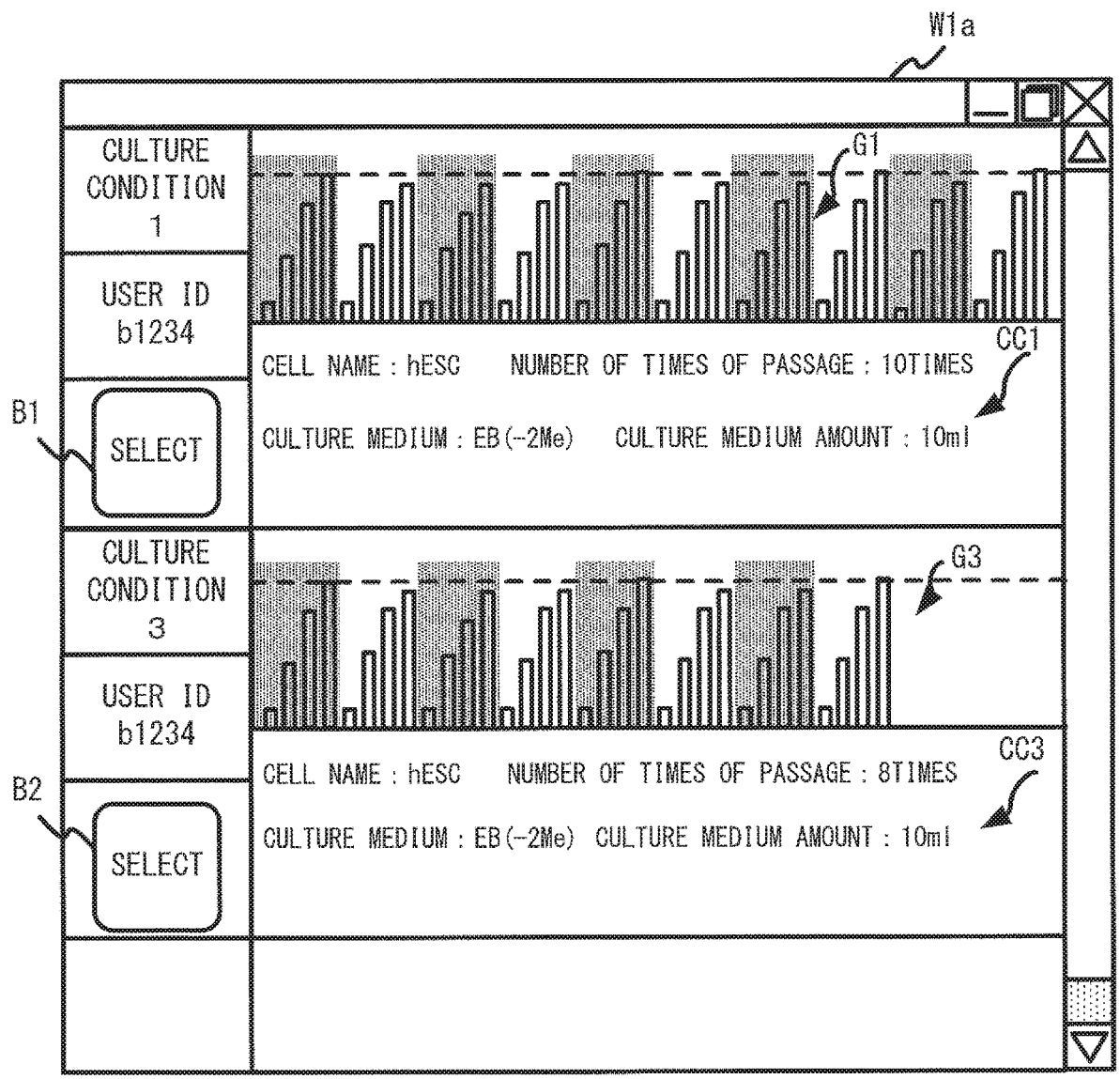
FIG. 13 illustrates another example of a culture-condition list window.

Culture-condition master table TBi2 illustrated in FIG. 12 may be built in the storage 113 instead of culture-condition master table TBi illustrated in FIG. 5. In that case, in step S51, the culture-condition display instruction is input to the control device 30 with the user specifying at least either the user ID or the date by using the input device 50. For example, when a culture-condition display instruction specifying the user ID has been input, the control device 30 may, in step S31b, specifies the user ID and outputs the request including the user ID, and may, in step S31d, list only culture conditions registered by specific users as illustrated in FIG. 13. This makes easy for a user to for example display only culture conditions registered by the user himself or herself.

Also, methods of identifying the culture condition of each culture vessel on the side of the microscope system 10 are not limited to the selection of a culture condition by the user. A culture condition may be identified through the vessel identification information assigned to the culture vessel. Vessel identification information is for example a bar code, a QR code, and information stored in an IC tag such as an RF tag etc., and is information for identifying a culture vessel.

In such a case, the vessel identification information of the culture vessel is in advance read by a vessel identification information reading unit 140, illustrated in FIG. 1, that is provided on the side of the culture monitoring system 100, the read vessel identification information is in advance stored in association with the culture condition of that culture vessel. The vessel identification information reading unit 140 is for example a bar-code reader, a QR-code reader, and an IC-tag reader connected to the control device 110.

More specifically, the vessel identification information may be stored in culture-condition master table TBi illustrated in FIG. 5 so as to be associated with the culture condition identified by the UUID. Also, vessel identification information may be stored in a table different from culture-condition master table TBi in association with the UUID of the culture condition so as to be associated with the culture condition.

In the analysis preparation process, a vessel identification information reading unit 60, illustrated in FIG. 1, provided in the microscope system 10 reads the vessel identification information of the culture vessel mounted on the stage 21 of the microscope apparatus 20. Note that the vessel identification information reading unit 60 is for example a bar-code reader, a QR-code reader, an IC tag reader connected to the control device 30. Thereby, the control device 30 can use the vessel identification information read by the vessel identification information reading unit 60 to identify the corresponding culture condition in culture-condition master table TBi built in the control device 110. In other words, the control device 30 can obtain the culture condition corresponding to the vessel identification information from the culture monitoring system 100 on the basis of the vessel identification information.

Thus, the use of vessel identification information eliminates the necessity for the user to search for and select the corresponding culture condition from among a plurality of culture conditions displayed on the display device 40 as illustrated in FIG. 7.

Note that when a microscope observation is to be performed after transferring a culture cell from the culture vessel that has been used for culturing the culture cell during that culturing in the culture monitoring system 100 to a different sample vessel suitable for the microscope observation, the same vessel identification information as that of the culture vessel is assigned to the sample vessel that is to be used for the microscope observation.

Note that the vessel identification information of a culture vessel may be associated with the UUID of a microscopic image stored in the microscopic image table illustrated in FIG. 10.

Second Embodiment

Figure 14:
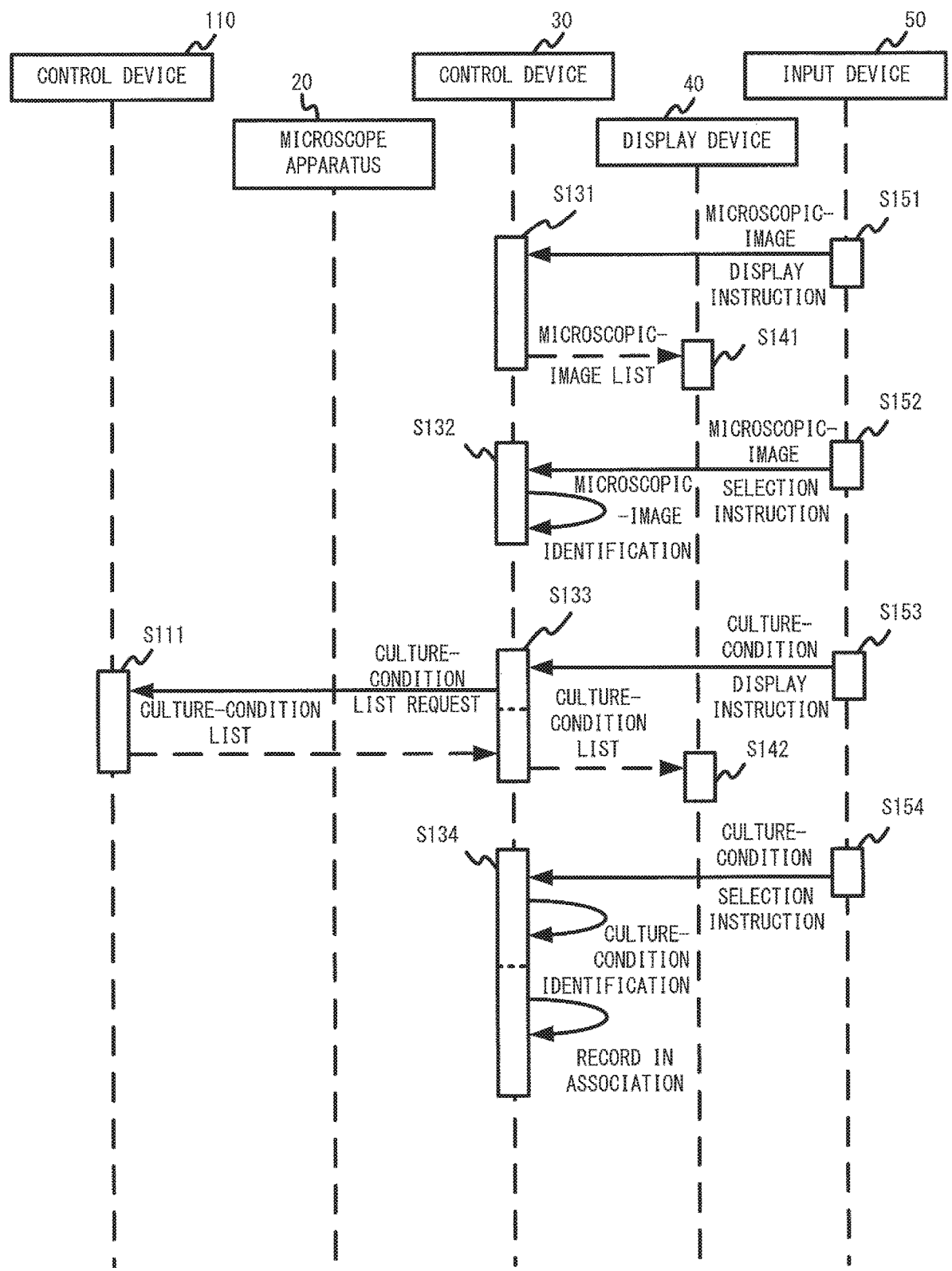
FIG. 14 illustrates an example of a sequence diagram according to the second embodiment.
Figure 15:
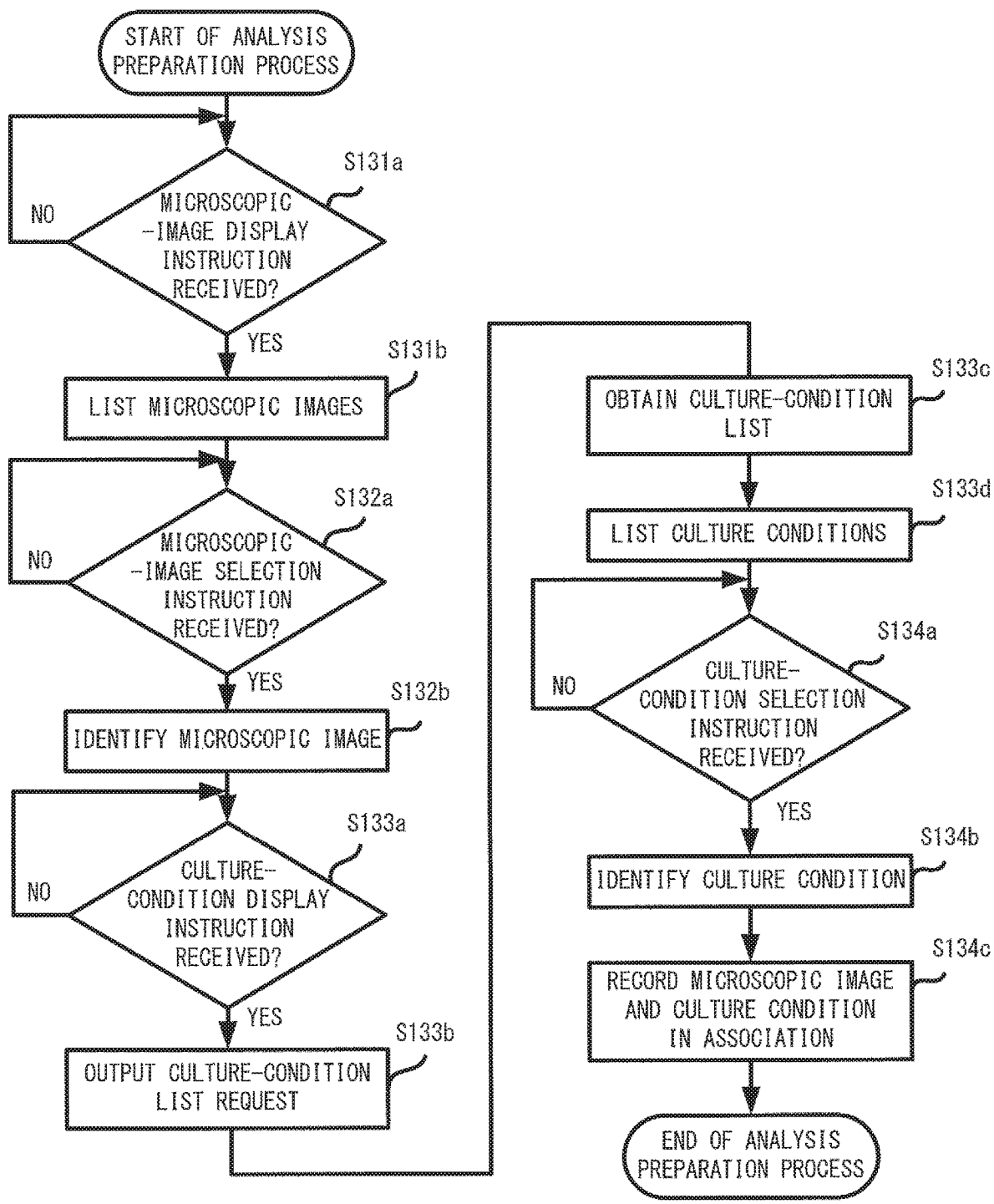
FIG. 15 illustrates an example of a flowchart of an analysis preparation process according to the second embodiment.
Figure 17:
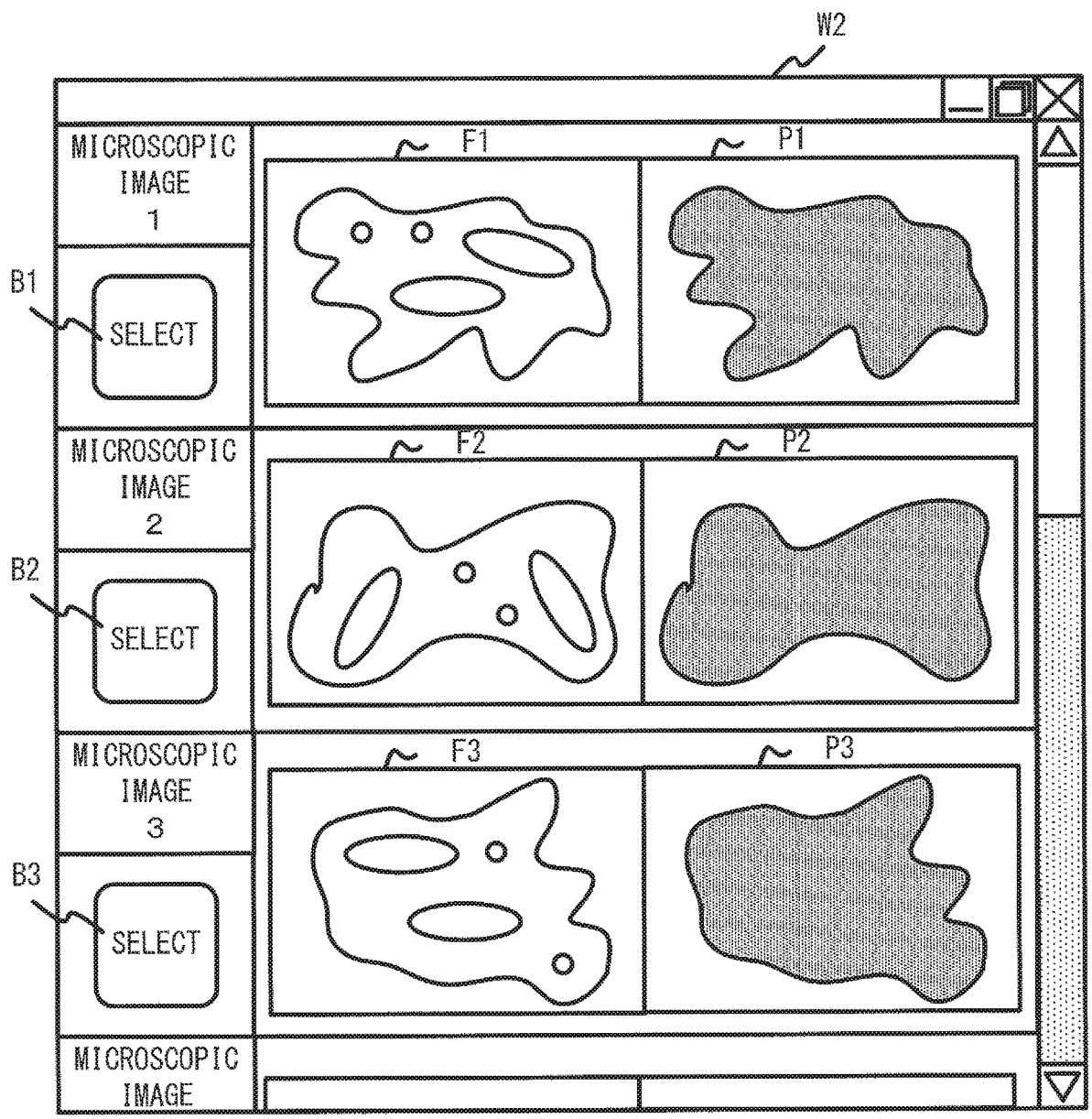
FIG. 17 illustrates an example of a microscopic-image list window.

FIG. 14 illustrates an example of a sequence diagram according to the second embodiment. FIG. 15 illustrates an example of a flowchart of an analysis preparation process according to the second embodiment. FIG. 16 illustrates another example of a microscopic-image table. FIG. 17 illustrates an example of a microscopic-image list window.

The analysis preparation process according to the present embodiment is greatly different from the analysis preparation process according to the first embodiment in that it starts with at least one microscopic image obtained in advance and being in a recorded state in microscopic-image table TBm3 as illustrated in FIG. 16. By referring to FIG. 14 through FIG. 17, explanations will hereinafter be given for the analysis preparation process according to the present embodiment that is performed by the control device 30 of the culture-cell analysis system 1.

First, the user uses the input device 50 to input a microscopic-image display instruction to the control device 30 (step S151). This starts the analysis preparation process illustrated in FIG. 15 in the control device 30.

When receiving the microscopic-image display instruction from the input device 50 (YES in step S131a), the control device 30 makes the display device 40 list the microscopic image read from microscopic-image table TBm3 (step S131b). Thereby, the display device 40 displays microscopic-image list window W2 illustrated in FIG. 17 (step S141).

Microscopic-image list window W2 illustrated in FIG. 17 is an example of a window that is generated by the control device 30 on the basis of a list of microscopic images read out to the memory 32 from microscopic-image table TBm3 and that is displayed by the display device 40. Window W2 includes fluorescence images (fluorescence images F1 through F3) and phase-contrast images (phase-contrast images P1 through P3).

Next, the user uses the input device 50 to select a microscopic image that is to be associated with the culture condition from among the microscopic images listed in window W2, and thereby inputs a microscopic-image selection instruction to the control device 30 (step S152). In this example, the user pushes button B1 in window W2, and thereby selects "microscopic image 1" (fluorescence image F1 and phase-contrast image P1).

When receiving the microscopic-image selection instruction from the input device 50 (YES in step S132a), the control device 30 identifies, from among the microscopic images stored in the memory 32, the microscopic image selected by the user (step S132b). The microscopic image identified in step S132b will hereinafter be referred to as a second microscopic image.

The user thereafter uses the input device 50 to input the culture-condition display instruction to the control device 30 (step S153). When receiving the culture-condition display instruction from the input device 50 (YES in step S133a), the control device 30 outputs a culture-condition list request 110 (step S133b). The control device 110 that has received the culture-condition list request outputs, to the control device 30, the culture-condition list read from culture-condition master table TBi (step S111). When receiving the culture-condition list from the control device 110 (step S133c), the control device 30 stores the obtained culture conditions in the memory 32, and thereafter makes the display device 40 list the culture conditions (step S133d). The display device 40 thus displays culture-condition list window W1 illustrated in FIG. 7 (step S142). Note that the processes from step S153 through step S141 are similar to those of step S51 through step S41 in FIG. 3.

Next, the user uses the input device 50 to select a culture condition corresponding to the microscopic image identified in step S132b (namely, the second microscopic image selected by the user), from among the culture conditions listed in window W1, and thereby inputs the culture-condition selection instruction to the control device 30 (step S154). In this example, the user pushes button B1 in window W1, and thereby selects "culture condition 1".

When receiving the culture-condition selection instruction from the input device 50 (YES in step S134a), the control device 30 identifies, from among the culture conditions stored in the memory 32, the culture condition selected by the user (step S134b). The culture condition identified in step S134b will hereinafter be referred to as a second culture condition.

The control device 30 further records the second microscopic image and the second culture condition in association with each other (step S134c), the second microscopic image being identified in step S132b and the second culture condition being identified in step S134b. In step S134c, the second culture condition to be recorded in association with the second microscopic image is recorded in culture-condition table TBm2, the UUIDs of the second microscopic image and the second culture condition are further recorded in link table TBm1, and thereby the second microscopic image and the second culture condition are associated with each other.

Performing the analysis preparation process according to the present embodiment as well enables the microscope system 10 to record a microscopic image obtained by the microscope apparatus 20 and a culture condition in association with each other. The present embodiment thus can achieve an effect similar to that of the first embodiment. Also, the analysis preparation process according to the present embodiment imposes less limitation about when to obtain a microscopic image than the first embodiment, in which a microscopic image is obtained when the association is performed. Thereby, association can be performed for a microscopic image that was obtained in the past, making it possible to utilize existing data efficiently.

Third Embodiment

Figure 18:
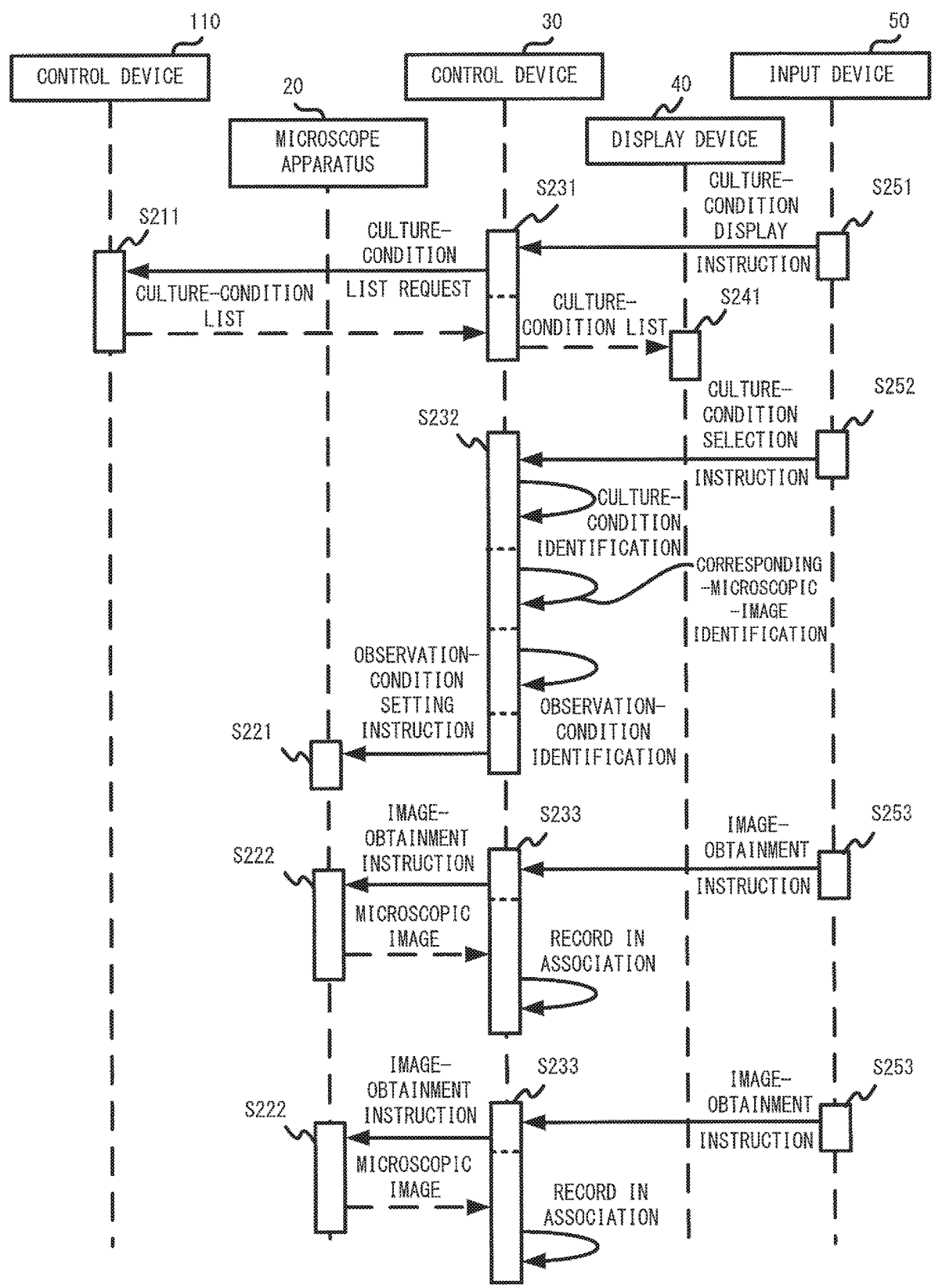
FIG. 18 illustrates an example of a sequence diagram according to the third embodiment.
Figure 19:
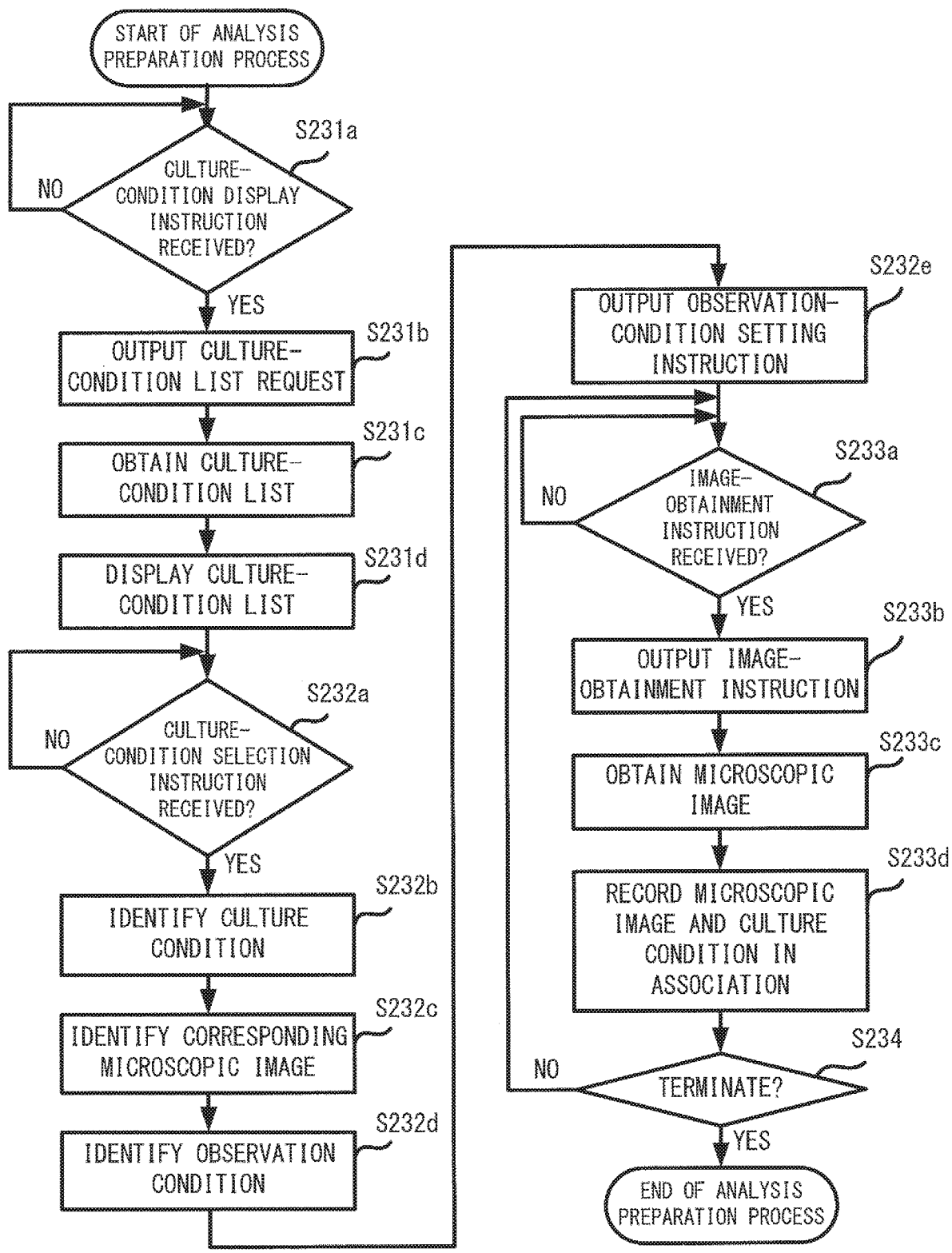
FIG. 19 illustrates an example of a flowchart of an analysis preparation process according to the third embodiment.

FIG. 18 illustrates an example of a sequence diagram according to the third embodiment. FIG. 19 illustrates an example of a flowchart of an analysis preparation process according to the third embodiment.

The analysis preparation process according to the present embodiment is greatly different from the analysis preparation process according to the first embodiment in that it starts in a state in which each of the culture conditions recorded in culture-condition master table TBi is already in association with at least one microscopic image in link table TBm1. By referring to FIG. 18 and FIG. 19, explanations will hereinafter be given for the analysis preparation process according to the present embodiment performed by the control device 30 of the culture-cell analysis system 1.

First, the user uses the input device 50 to input a culture-condition display instruction to the control device 30 (step S251). This starts the analysis preparation process illustrated in FIG. 19 in the control device 30.

When receiving the culture-condition display instruction from the input device 50 (YES in step S231a), the control device 30 outputs a culture-condition list request to the control device 110 (step S231b). The control device 110 that has received a culture-condition list request outputs, to the control device 30, the culture-condition list read from culture-condition master table TBi (step S211). When obtaining the culture-condition list from the control device 110 (step S231c), the control device 30 stores the obtained culture conditions in the memory 32, and makes the display device 40 list the culture conditions (step S231d). Thereby, the display device 40 displays culture-condition list window W1 illustrated in FIG. 7 (step S241). Note that the processes from step S251 through step S241 are similar to those of step S51 through step S41 in FIG. 3.

Next, the user uses the input device 50 to select the culture condition corresponding to culture vessel D1 (culture cell C) mounted on the stage 21 of the microscope apparatus 20, from among the culture conditions listed in window W1, and thereby inputs the culture-condition selection instruction to the control device 30 (step S252). In this example, the user for example pushes button B1 in window W1 to select "culture condition 1".

When receiving the culture-condition selection instruction from the input device 50 (YES in step S232a), the control device 30 identifies, from among the culture conditions stored in the memory 32, the culture condition selected by the user (step S232b). The culture condition identified in step S232b will hereinafter be referred to as a third culture condition.

The control device 30 further identifies the microscopic image corresponding to the identified third culture condition (step S232c). Note that "microscopic image corresponding to a third culture condition" refers to the microscopic image recorded in association with the third culture condition in link table TBm1, and will hereinafter be referred to as a third microscopic image. In other words, the control device 30 in step S232c searches link table TBm1 by using, as the key, the UUID of the culture condition identified in step S232b so as to identify the third microscopic image corresponding to the third culture condition.

When the third microscopic image is identified, the control device 30 identifies the observation condition corresponding to the identified third microscopic image (step S232d). Note that "observation condition" refers to a setting item for a microscope apparatus that influences the microscopic image, and examples thereof include observation magnification and a brightness setting. Also, "observation condition corresponding to a third microscopic image" refers to the observation condition set in the microscope apparatus 20 when the microscope apparatus 20 obtained the third microscopic image. When an observation condition is embedded in a third microscopic image, the observation condition corresponding to the third microscopic image may be extracted from the data of the third microscopic image so as to identify the observation condition. When the table for associating a microscopic image and an observation condition has been built in the control device 30, an observation condition may be identified by referring to that table.

When the observation condition is identified, the control device 30 outputs an observation-condition setting instruction to the microscope apparatus 20 (step S232e). Specifically, the control device 30 controls the microscope apparatus 20 so that the observation condition identified in step S232d is set in the microscope apparatus 20. Thereby, the microscope apparatus 20 sets the observation condition identified in step S232d (step S221).

The user thereafter uses the input device 50 to input an image-obtainment instruction to the control device 30 (step S253).

When receiving the image-obtainment instruction from the input device 50 (YES in step S233a), the control device 30 outputs the image-obtainment instruction to the microscope apparatus 20 (step S233b).

The microscope apparatus 20 that has received the image-obtainment instruction picks up an image of culture cell C so as to obtain a fluorescence image and a phase-contrast image as microscopic images of culture cell C, and outputs these images to the control device 30 (step S222). Note that the microscopic image output to the control device 30 in step S222 is the fourth microscopic image obtained by the microscope apparatus 20 after the observation condition identified in step S232d is set in the microscope apparatus 20.

When obtaining the fourth microscopic image from the microscope apparatus 20 (step S233c), the control device 30 records the obtained fourth microscopic image and the third culture condition identified in step S232b in association with each other (step S233d). Specifically, in step S233d, the fourth microscopic image and the third culture condition that are to be recorded in association with each other are recorded in microscopic-image table TBm3 and culture-condition table TBm2, the UUIDs of the fourth microscopic image and the third culture condition are further recorded in link table TBm1, and thereby the fourth microscopic image and the third culture condition are associated with each other.

Lastly, the control device 30 determines whether to terminate the analysis preparation process (step S234). In this determination, the control device 30 determines not to terminate the analysis preparation process when a termination instruction has not been input from the input device 50, and repeats the processes in step S233a through step S234. Meanwhile, when a termination instruction has been input from the input device 50, the control device 30 terminates the analysis preparation process.

Performing the analysis preparation process according to the present embodiment as well enables the microscope system 10 to record a microscopic image obtained by the microscope apparatus 20 and a culture condition in association with each other. The present embodiment thus can achieve an effect similar to that of the first embodiment. The analysis preparation process according to the present embodiment also makes it possible to obtain a new microscopic image under the same culture condition and the same observation condition as those for a microscopic image which have already been obtained. This enables comparison between microscopic images obtained under the same condition, making it possible to perform analysis that is influenced by neither a culture condition nor an observation condition.

Fourth Embodiment

Figure 20:
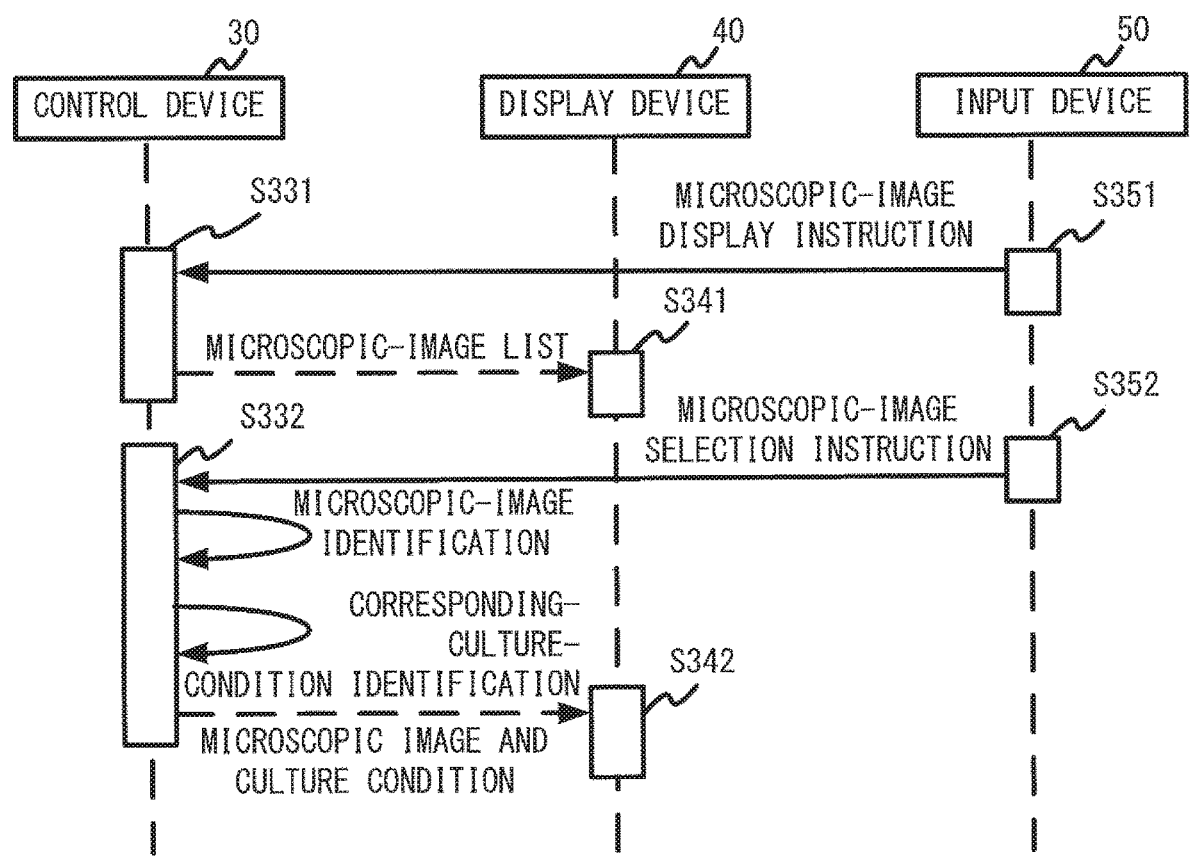
FIG. 20 illustrates an example of a sequence diagram according to the fourth embodiment.
Figure 21:
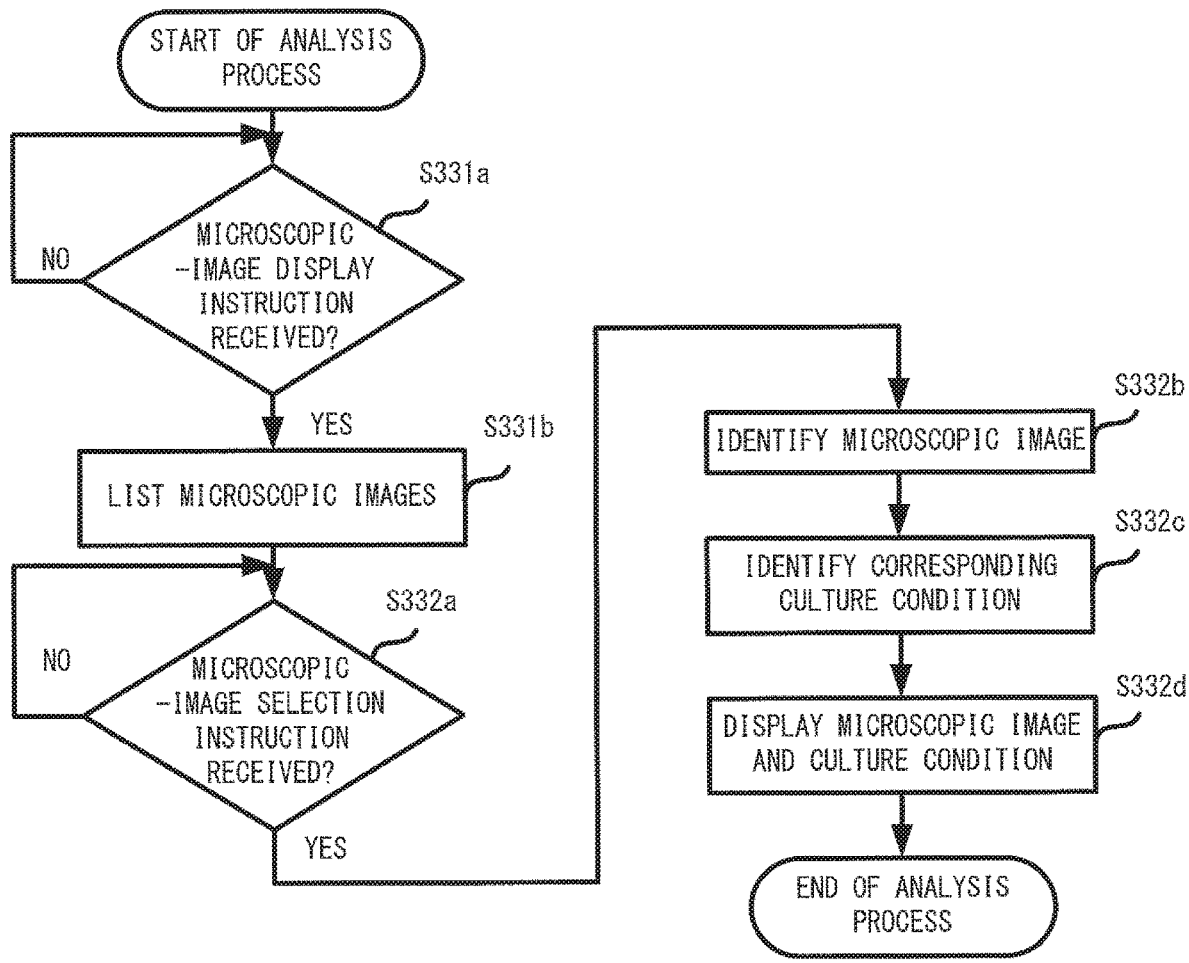
FIG. 21 illustrates an example of a flowchart of an analysis process according to the fourth embodiment.
Figure 22:
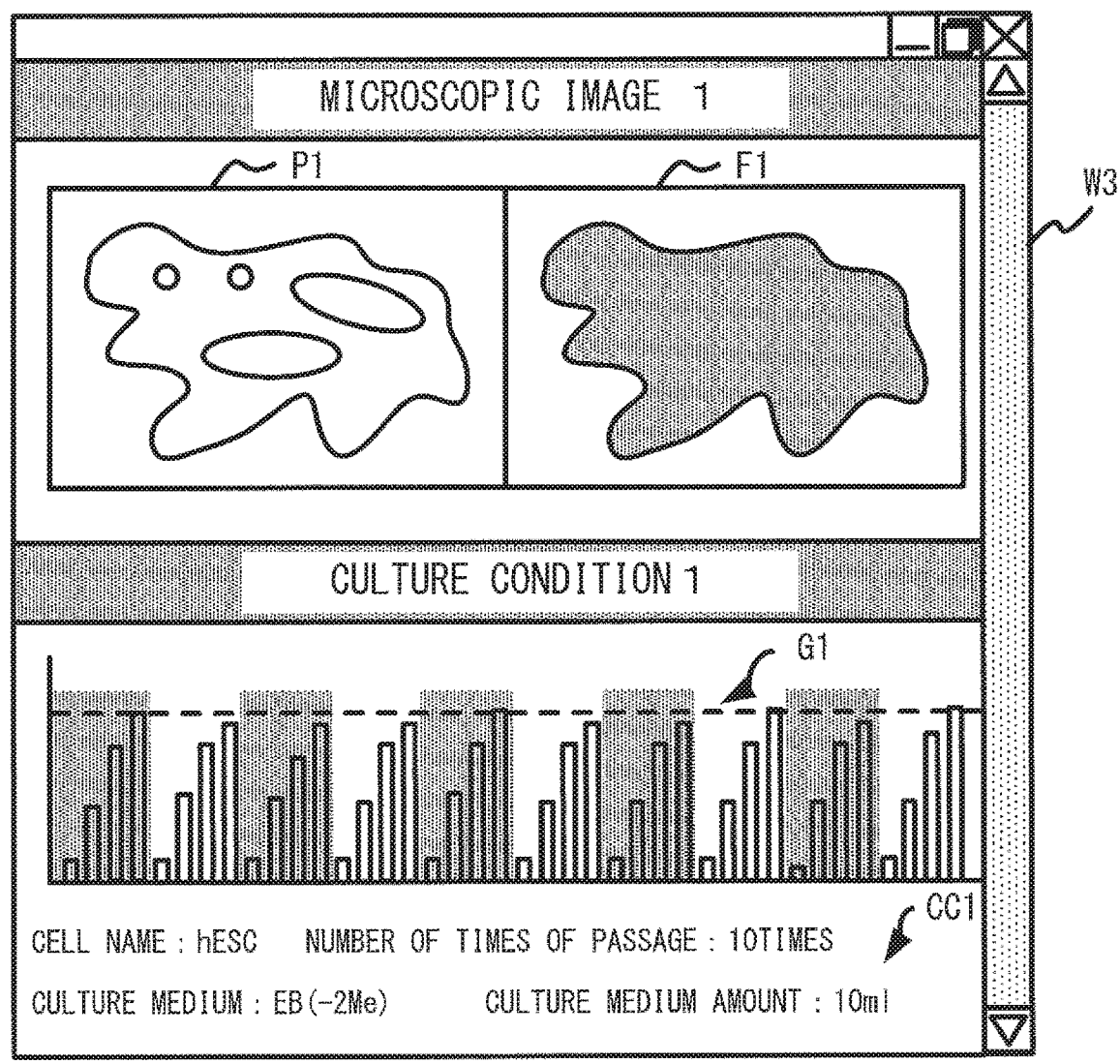
FIG. 22 illustrates an example of an analysis window.

FIG. 20 illustrates an example of a sequence diagram according to the fourth embodiment. FIG. 21 illustrates an example of a flowchart of an analysis process according to the fourth embodiment. FIG. 22 illustrates an example of an analysis window. By referring to FIG. 20 through FIG. 22, explanations will be given for the analysis process according to the present embodiment that is performed by the control device 30 of the culture-cell analysis system 1. Note that the analysis process is performed after the culture condition and the microscopic image are associated with each other by the analysis preparation process. This applies also to the fifth and sixth embodiments, which will be explained later.

First, the user uses the input device 50 to input a microscopic-image display instruction to the control device 30 (step S351). This starts the analysis process illustrated in FIG. 21 in the control device 30.

When receiving the microscopic-image display instruction from the input device 50 (YES in step S331a), the control device 30 stores, in the memory 32, the microscopic images read from microscopic-image table TBm3, and further makes the display device 40 list the microscopic images (step S331b). Thereby, the display device 40 displays microscopic-image list window W2 illustrated in FIG. 17 (step S341).

Next, the user uses the input device 50 to select a microscopic image that is to be displayed for the analysis from among the microscopic images listed in window W2, and thereby inputs the microscopic-image selection instruction to the control device 30 (step S352). In this example, the user pushes button B1 in window W2 to select "microscopic image 1" (fluorescence image F1 and phase-contrast image P1).

When receiving the microscopic-image selection instruction from the input device 50 (YES in step S332a), the control device 30 identifies, from among the microscopic images stored in the memory 32, the microscopic image selected by the user (step S332b).

The control device 30 further identifies the culture condition corresponding to the identified microscopic image (step S332c). Note that "culture condition corresponding to a microscopic image" refers to the culture condition recorded in association with the microscopic image in link table TBm1. In other words, the control device 30 in step S332c searches link table TBm1 by using, as the key, the UUID of the microscopic image identified in step S332b so as to identify the culture condition corresponding to the microscopic image.

Lastly, the control device 30 makes the display device 40 display both the microscopic image and the culture condition, the microscopic image being identified in step S332b and the culture condition being identified in step S332c (step S332d). Thereby, the display device 40 displays analysis window W3 illustrated in FIG. 22 (step S342).

Analysis window W3 illustrated in FIG. 22 is an example of a window that is generated on the basis of the microscopic image identified in step S332b and the culture condition identified in step S332c and that is displayed by the display device 40. Window W3 includes microscopic images (fluorescence image F1 and phase-contrast image P1) and a culture condition (graph image G1 and character information CC1).

As described above, performing the analysis process according to the present embodiment enables the microscope system 10 to make the display device 40 display a microscopic image obtained by the microscope apparatus 20, together with the culture condition for the culture cell appearing in that microscopic image. This makes it easy for the user to check the culture condition for the culture cell while viewing the microscopic image. The microscope system 10 and the culture monitoring system 100 according to the present embodiment thus can assist the analysis of a culture cell by for example making it easy to determine whether the culture condition has influenced an image of the culture cell when the image of the culture cell is different from the expected image.

Fifth Embodiment

Figure 23:
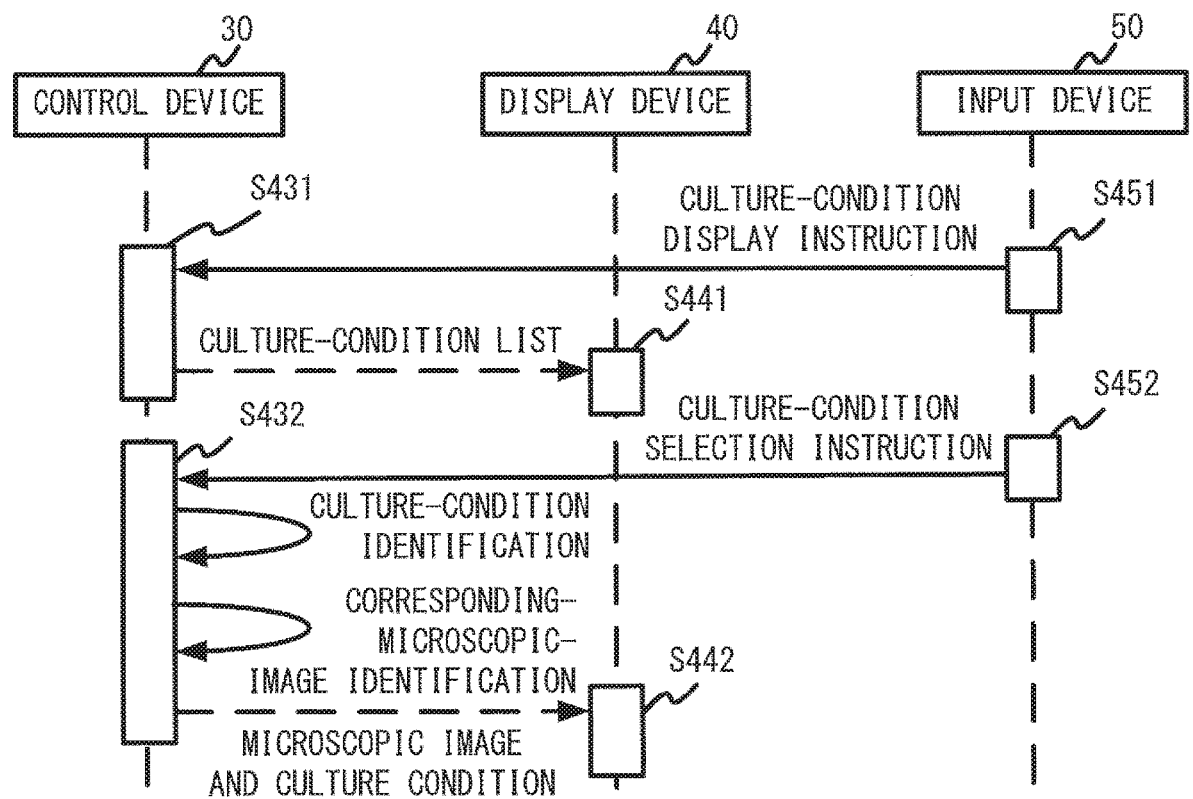
FIG. 23 illustrates an example of a sequence diagram according to the fifth embodiment.
Figure 24:
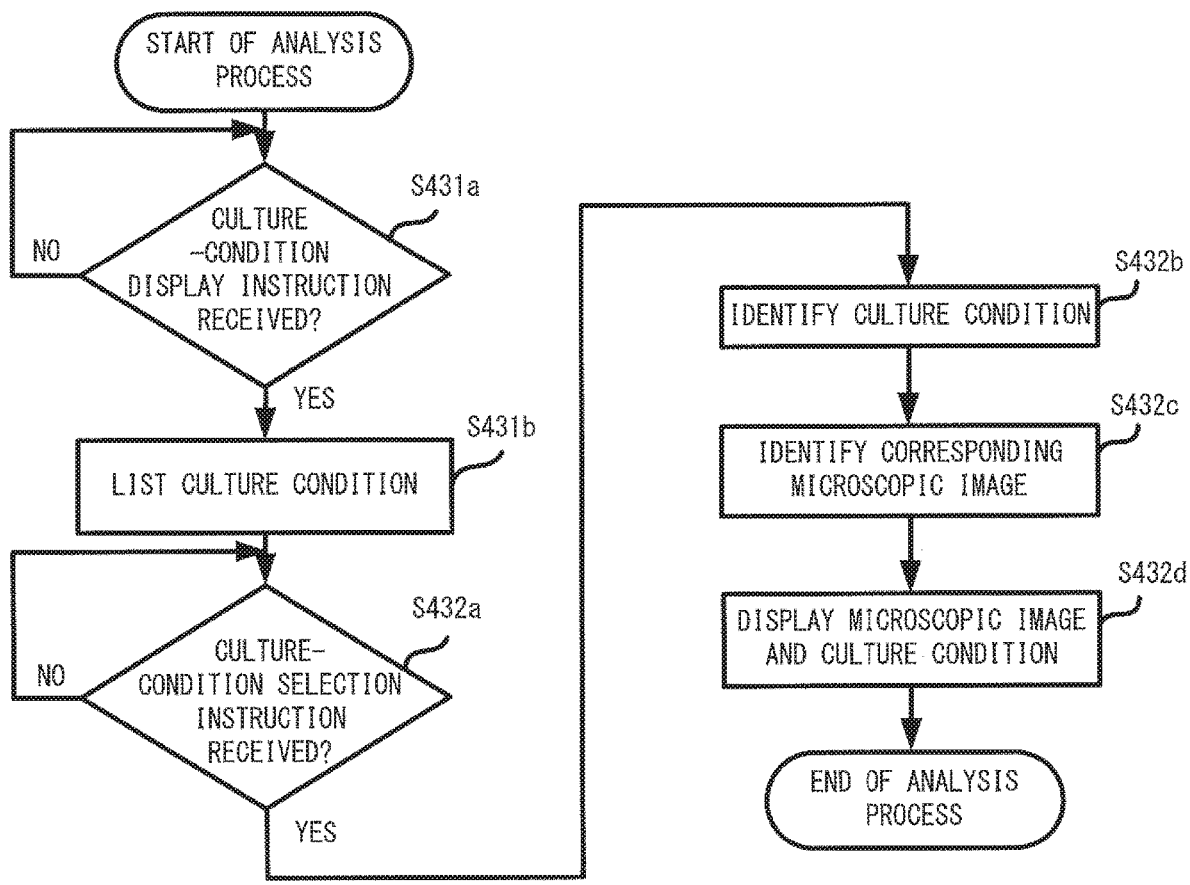
FIG. 24 is an example of a flowchart for an analysis process according to the fifth embodiment.

FIG. 23 illustrates an example of a sequence diagram according to the fifth embodiment. FIG. 24 is an example of a flowchart for an analysis process according to the fifth embodiment. The analysis process according to the present embodiment is different from the analysis process according to the fourth embodiment in that it selects a culture condition from between the microscopic image and the culture condition that are recorded in association with each other. In other words, at least one of a microscopic image and a culture condition recorded in association with each other is selected in the microscope system 10 as explained in the fourth embodiment and the present embodiment. By referring to FIG. 23 and FIG. 24, explanations will hereinafter be given for the analysis process according to the present embodiment that is performed by the control device 30 of the culture-cell analysis system 1.

First, the user uses the input device 50 to input a culture-condition display instruction to the control device 30 (step S451). This starts the analysis process illustrated in FIG. 24 in the control device 30.

When receiving the culture-condition display instruction from the input device 50 (YES in step S431a), the control device 30 stores, in the memory 32, the culture conditions read from culture-condition table TBm2, and further makes the display device 40 list the culture conditions (step S431b). Thereby, the display device 40 displays culture-condition list window W1 illustrated in FIG. 7 (step S441).

Next, the user uses the input device 50 to select a culture condition that is to be displayed for the analysis from among the culture conditions listed in window W1, and thereby inputs the culture-condition selection instruction to the control device 30 (step S452). In this example, the user pushes button B1 in window W1 to select "culture condition 1".

When receiving the culture-condition selection instruction from the input device 50 (YES in step S432a), the control device 30 identifies, from among the culture conditions stored in the memory 32, the culture condition selected by the user (step S432b).

The control device 30 further identifies the microscopic image corresponding to the identified culture condition (step S432c). Note that "microscopic image corresponding to a culture condition" refers to the microscopic image recorded in association with the culture condition in link table TBm1. In other words, the control device 30 in step S432c searches link table TBm1 by using, as the key, the UUID of the culture condition identified in step S432b so as to identify the microscopic image corresponding to the culture condition.

Lastly, the control device 30 makes the display device 40 display both the culture condition and the microscopic image, the culture condition being identified in step S432b and the microscopic image being identified in step S432c (step S432d). Thereby, the display device 40 displays analysis window W3 illustrated in FIG. 22 (step S442).

Performing the analysis process according to the present embodiment as well enables the microscope system 10 to make the display device 40 display a microscopic image obtained by the microscope apparatus 20, together with the culture condition for the culture cell appearing in that microscopic image. The present embodiment thus can achieve an effect similar to that of the fourth embodiment. Note that when a plurality of microscopic images are recorded in association with the selected culture condition, the culture condition may be displayed together with the plurality of microscopic images.

Sixth Embodiment

Figure 25:
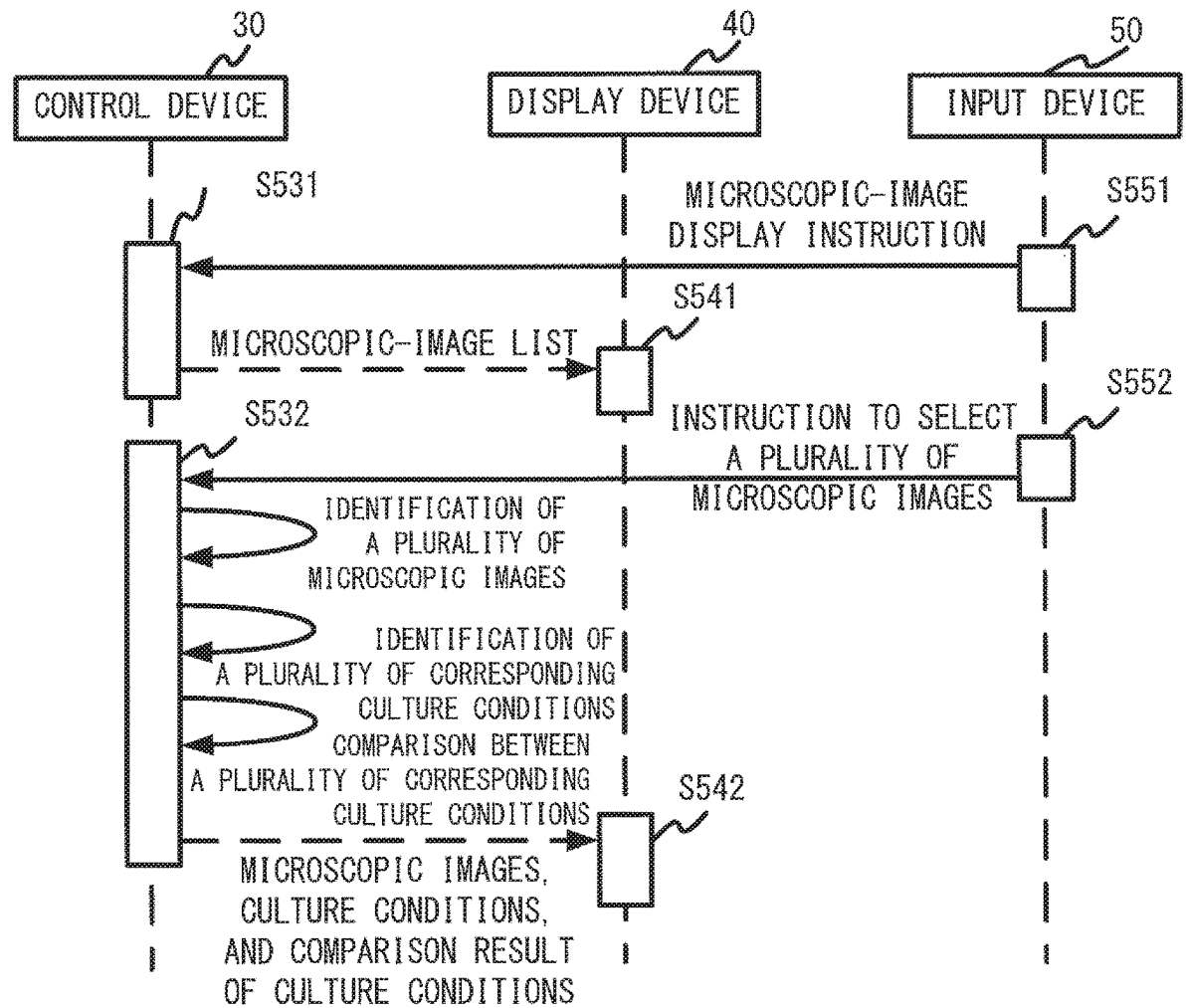
FIG. 25 illustrates an example of a sequence diagram according to the sixth embodiment.
Figure 26:
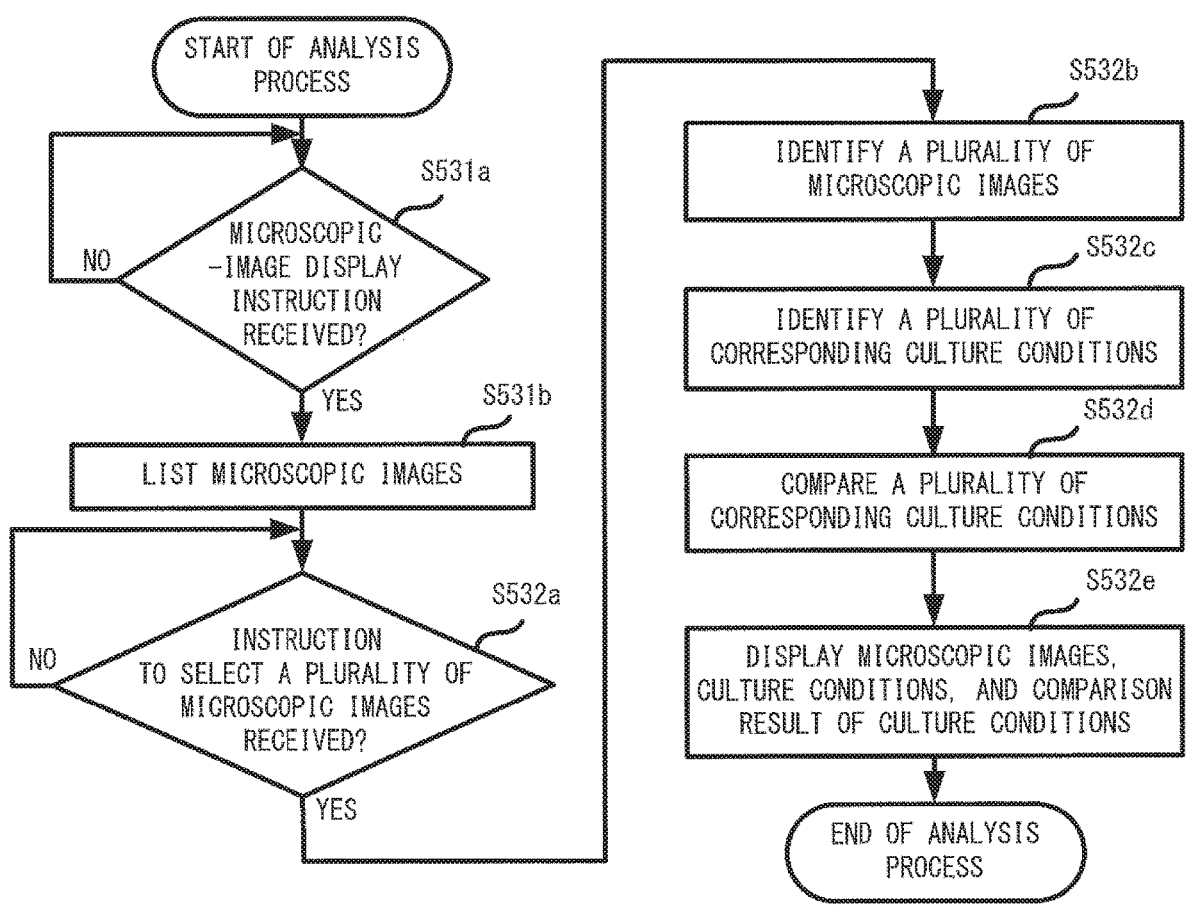
FIG. 26 illustrates an example of a flowchart of an analysis process according to the sixth embodiment.
Figure 27:
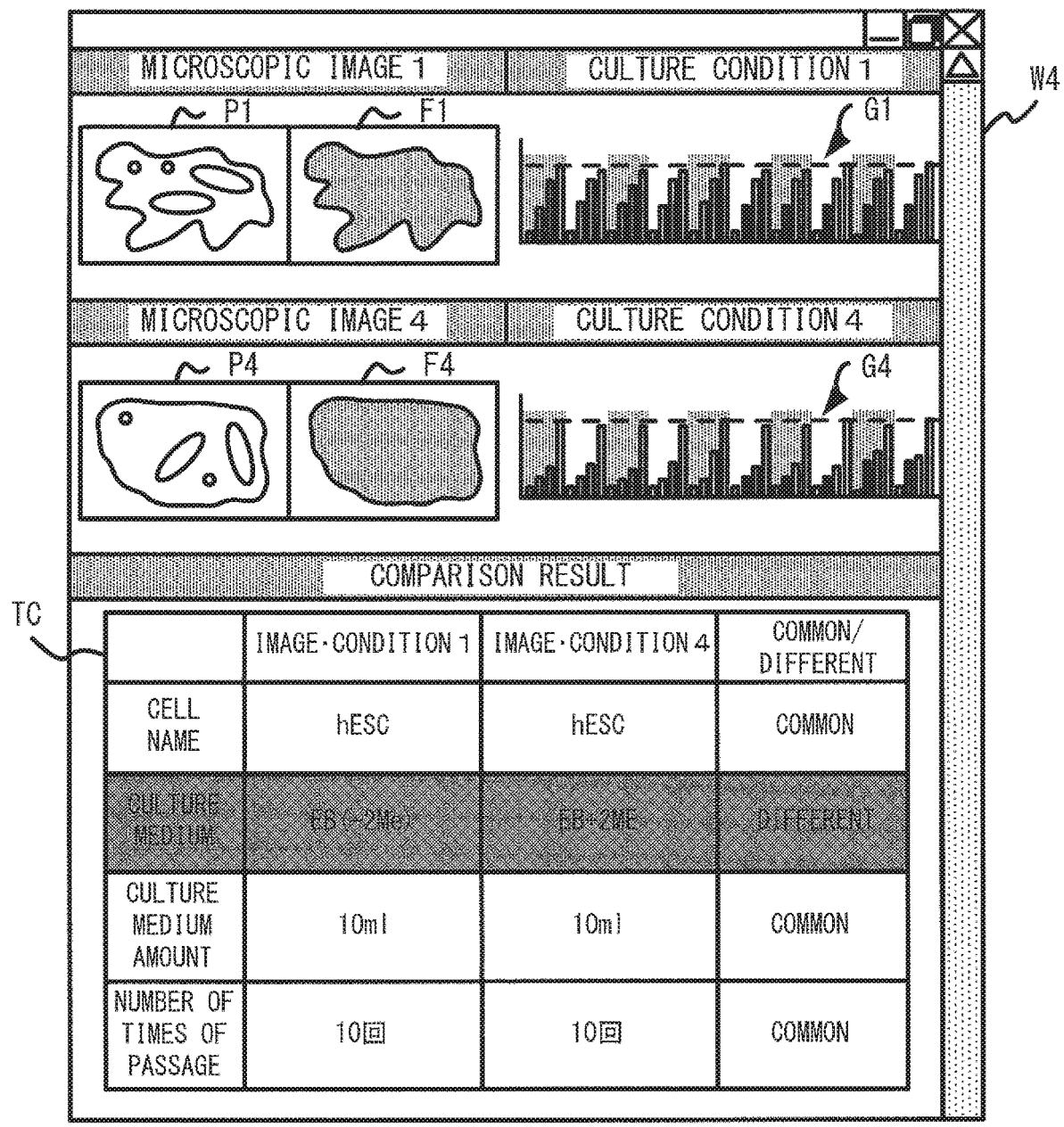
FIG. 27 illustrates another example of an analysis window.

FIG. 25 illustrates an example of a sequence diagram according to the sixth embodiment. FIG. 26 illustrates an example of a flowchart of an analysis process according to the sixth embodiment. FIG. 27 illustrates another example of an analysis window. The analysis process according to the present embodiment is different from the analysis process according to the fourth embodiment in that it selects a plurality of microscopic images from among the listed microscopic images. By referring to FIG. 25 through FIG. 27, explanations will be given for the analysis process according to the present embodiment that is performed by the control device 30 of the culture-cell analysis system 1.

First, the user uses the input device 50 to input a microscopic-image display instruction to the control device 30 (step S551). This starts the analysis process illustrated in FIG. 26 in the control device 30.

When receiving the microscopic-image display instruction from the input device 50 (YES in step S531a), the control device 30 stores, in the memory 32, the microscopic images read from microscopic-image table TBm3, and further makes the display device 40 list the microscopic images (step S531b). Thereby, the display device 40 displays microscopic-image list window W2 illustrated in FIG. 17 (step S541).

Next, the user uses the input device 50 to select a plurality of microscopic images that are to be displayed for the analysis from among the microscopic images listed in window W2, and thereby inputs the microscopic-image selection instruction to the control device 30 (step S552). In this example, the user pushes button B1 and button B4 in window W2 to select "microscopic image 1" (fluorescence image F1 and phase-contrast image P1) and "microscopic image 4" (fluorescence image F4 and phase-contrast image P4).

When receiving the microscopic-image selection instruction to select a plurality of microscopic images from the input device 50 (YES in step S532a), the control device 30 identifies, from among the microscopic images stored in the memory 32, the plurality of microscopic images selected by the user (step S532b).

The control device 30 further identifies the plurality of culture conditions corresponding to the plurality of identified microscopic images (step S532c). In other words, the control device 30 in step S532c searches link table TBm1 by using, as the key, the UUIDs of the plurality of microscopic images identified in step S532b so as to identify the plurality of culture conditions corresponding to the plurality of microscopic images.

When the plurality of culture conditions are identified, the control device 30 compares the plurality of culture conditions (step S532d), and generates a comparison result in the form of for example a table, i.e., a comparison table. Lastly, the control device 30 makes the display device 40 display the plurality of microscopic images identified in step S532b, the plurality of culture conditions identified in step S532c, and the comparison result generated in step S532d (step S532e). Thereby, the display device 40 displays analysis window W4 illustrated in FIG. 27 (step S542).

Note that comparison table TC illustrated in FIG. 27 is an example of the comparison result generated in step S532d. Specifically, the display device 40 displays the comparison result of a plurality of culture conditions associated with the plurality of selected microscopic images in step S542. The comparison result includes at least a different portion; however the comparison result may include a common portion and a different portion as illustrated in FIG. 27. When a common portion and a different portion are included, the common portion and the different portion may be displayed in different manners (different in color, size, etc. for example) in order to facilitate distinguishing between the common portion and the different portion as illustrated in FIG. 27.

Performing the analysis process according to the present embodiment as well enables the microscope system 10 to make the display device 40 display a microscopic image obtained by the microscope apparatus 20, together with the culture condition for the culture cell appearing in that microscopic image. The present embodiment thus can achieve an effect similar to that of the fourth embodiment. Further, according to the analysis process of the present invention, just selecting a plurality of microscopic images displays the comparison result of a plurality of culture conditions for a culture cell appearing in a plurality of microscopic images. This makes it possible to check the influence of a different between culture conditions on the image.

The above embodiments are specific examples for facilitating understanding of the invention, and the embodiments of the present invention are not limited to the examples. The microscope system and the culture-cell analysis system allow various modifications and changes without departing from the claims.

For example, while the sixth embodiment illustrates an example in which a plurality of microscopic images are selected, a plurality of culture conditions may be selected instead of a plurality of microscopic images. In other words, it is sufficient if either a plurality of microscopic images or a plurality of culture conditions are selected.

What is claimed is:

1. A microscope system comprising:
   a microscope apparatus; and
   a first control device comprising a first hardware processor,
   wherein:
   the microscope apparatus is configured to obtain a microscopic image of a culture cell, which has been cultured in an incubator of a culture monitoring system, by picking up an image of the culture cell after the culture cell has been taken out from the incubator and moved to the microscope apparatus, the culture monitoring system being spatially separated from the microscope apparatus, the culture monitoring system including the incubator and a second control device comprising a second hardware processor, and the culture monitoring system being configured to monitor a culture status of the culture cell, and
   the first control device is configured to record, in a recording unit in association with each other, (i) a culture condition of the culture cell under which the culture cell was cultured in the incubator before being taken out from the incubator and moved to the microscope apparatus, and (ii) the microscopic image, and manage the microscope image based on the recording in the recording unit.

2. The microscope system according to claim 1, wherein the first control device makes a display device display at least one culture condition obtained from the culture monitoring system, and records the culture condition and the microscopic image in the recording unit in association with each other, the culture condition being a first culture condition identified from among the at least one culture condition in accordance with a selection by a user of the microscope system.

3. The microscope system according to claim 2, wherein the first control device makes the display device display both the culture condition and the microscopic image when one of the culture condition and the microscopic image recorded in the recording unit in association with each other is selected.

4. The microscope system according to claim 1, wherein the culture condition includes at least one of an identifier of a user who registered the culture condition and a date of registration of the culture condition, and the first control device specifies at least one of the identifier of the user and the date, and
   makes a display device display at least one culture condition obtained from the culture monitoring system.

5. The microscope system according to claim 4, wherein the first control device records the culture condition and the microscopic image in the recording unit in association with each other, the culture condition being a first culture condition identified from among the at least one culture condition in accordance with a selection by a user of the microscope system.

6. The microscope system according to claim 5, wherein the first control device makes the display device display both the culture condition and the microscopic image when one of the culture condition and the microscopic image recorded in the recording unit in association with each other is selected.

7. The microscope system according to claim 4, wherein the first control device records the culture condition and the microscopic image in the recording unit in association with each other, the culture condition being a first culture condition identified from among the at least one culture condition in accordance with a selection by a user of the microscope system, and the microscopic image being a first microscopic image obtained by the microscope apparatus after identification of the first culture condition.

8. The microscope system according to claim 4, wherein the first control device records the culture condition and the microscopic image in the recording unit in association with each other, the culture condition being a second culture condition identified from among the at least one culture condition in accordance with a selection by a user of the microscope system, and the microscopic image being a second microscopic image identified from among at least one microscopic image obtained by the microscope apparatus, in accordance with a selection by the user.

9. The microscope system according to claim 4, wherein the first control device obtains, from the recording unit, a third microscopic image recorded in association with a third culture condition identified in accordance with a selection by a user of the microscope system from among the at least one culture condition, controls the microscope apparatus so that an observation condition under which the third microscopic image was obtained is set in the microscope apparatus, and records the culture condition and the microscopic image in the recording unit in association with each other, the culture condition being the third culture condition and the microscopic image being a fourth microscopic image obtained by the microscope apparatus after setting of the observation condition.

10. The microscope system according to claim 4, wherein the first control device makes the display device display both the culture condition and the microscopic image when one of the culture condition and the microscopic image recorded in the recording unit in association with each other is selected.

11. The microscope system according to claim 1, wherein the first control device makes a display device display at least one culture condition obtained from the culture monitoring system, and records the culture condition and the microscopic image in the recording unit in association with each other, the culture condition being a first culture condition identified from among the at least one culture condition in accordance with a selection by a user of the microscope system, and the microscopic image being a first microscopic image obtained by the microscope apparatus after identification of the first culture condition.

12. The microscope system according to claim 1, wherein the first control device makes a display device display at least one culture condition obtained from the culture monitoring system, and records the culture condition and the microscopic image in the recording unit in association with each other, the culture condition being a second culture condition identified from among the at least one culture condition in accordance with a selection by a user of the microscope system, and the microscopic image being a second microscopic image identified from among at least one microscopic image obtained by the microscope apparatus, in accordance with a selection by the user.

13. The microscope system according to claim 1, wherein the first control device makes a display device display at least one culture condition obtained from the culture monitoring system, obtains, from the recording unit, a third microscopic image recorded in association with a third culture condition identified in accordance with a selection by a user of the microscope system from among the at least one culture condition, controls the microscope apparatus so that an observation condition under which the third microscopic image was obtained is set in the microscope apparatus, and records the culture condition and the microscopic image in the recording unit in association with each other, the culture condition being the third culture condition and the microscopic image being a fourth microscopic image obtained by the microscope apparatus after setting of the observation condition.

14. The microscope system according to claim 1, further comprising a vessel identification information reader configured to read, from a culture vessel containing the culture cell, vessel identification information identifying the culture vessel,
wherein the first control device:
obtains a culture condition corresponding to the culture vessel from the culture monitoring system based on the vessel identification information, and
records the culture condition, which is a first culture condition obtained based on the vessel identification information, and the microscopic image in the recording unit in association with each other.

15. The microscope system according to claim 1, wherein the first control device makes a display device display both the culture condition and the microscopic image when one of the culture condition and the microscopic image recorded in the recording unit in association with each other is selected.

16. The microscope system according to claim 1, wherein when a plurality of culture conditions or a plurality of microscopic images recorded in the recording unit in association with each other are selected, the first control device makes the display device display a result of a comparison between the selected plurality of culture conditions or a result of a comparison between a plurality of culture conditions associated with the selected plurality of microscopic images.

17. A culture-cell analysis system comprising:
a microscope system that includes a microscope apparatus and a first control device comprising a first hardware processor; and
a culture monitoring system that includes an incubator and a second control device comprising a second hardware processor, the culture monitoring system being configured to monitor a culture status of a culture cell, and the culture monitoring system being spatially separated from the microscope apparatus,
wherein:
the microscope apparatus is configured to obtain a microscopic image of the culture cell, which has been cultured in the incubator, by picking up an image of the culture cell after the culture cell has been taken out from the incubator and moved to the microscope apparatus, and
the first control device is configured to record, in a recording unit in association with each other, (i) a culture condition of the culture cell under which the culture cell was cultured in the incubator before being taken out from the incubator and moved to the microscope apparatus, and (ii) the microscopic image, and manage the microscope image based on the recording in the recording unit.

18. The culture-cell analysis system according to claim 17, wherein: the culture monitoring system further includes an image pickup device that is arranged in the incubator,
the second control device is configured to control the image pickup device to pick up an image of the culture cell when the culture cell is arranged in the incubator, and
the second control device outputs, to the first control device and in response to a request from the first control device, the culture condition of the culture cell which is calculated based on the image obtained by the image pickup device.

19. The culture-cell analysis system according to claim 17, wherein the culture condition includes at least one of an identifier of a user who registered the culture condition and a date of registration of the culture condition, and the first control device specifies at least one of the identifier of the user and the date, and makes a display device display at least one culture condition obtained from the culture monitoring system.

20. The culture-cell analysis system according to claim 17, wherein the first control device makes a display device display at least one culture condition obtained from the culture monitoring system, and records the culture condition and the microscopic image in the recording unit in association with each other, the culture condition being a first culture condition identified from among the at least one culture condition in accordance with a selection by a user of the microscope system.

21. A method of managing a microscopic image, the method comprising, under control of a microscope system:
obtaining, by a microscope apparatus of the microscope system, a microscopic image of a culture cell, which has been cultured in an incubator of a culture monitoring system, by picking up an image of the culture cell after the culture cell has been taken out from the incubator and moved to the microscope apparatus, the culture monitoring system being spatially separated from the microscope apparatus and being configured to monitor a culture status of the culture cell;
recording, in a recording unit in association with each other, (i) a culture condition of the culture cell under which the culture cell was cultured in the incubator before being taken out from the incubator and moved to the microscope apparatus, and (ii) the microscopic image; and
managing the microscope image based on the recording in the recording unit.

* * * * *